United States Patent [19]

Ito et al.

[11] Patent Number: 5,508,461
[45] Date of Patent: Apr. 16, 1996

[54] OPTICALLY ACTIVE 1-PHENYL-2-SUBSTITUTED PROPANE DERIVATIVES AND METHODS OF PRODUCING THE SAME

[75] Inventors: Michio Ito, Arai; Noritsugu Yamasaki, Tsukuba; Yoshinori Kobayashi, Joetsu; Kiyoshi Ikura, Tsukuba, all of Japan

[73] Assignee: Daicel Chemical Industries, Ltd., Osaka, Japan

[21] Appl. No.: 252,994

[22] Filed: Jun. 2, 1994

[30] Foreign Application Priority Data

Jun. 4, 1993 [JP] Japan ................................ 5-160225
Sep. 16, 1993 [JP] Japan ................................ 5-255085

[51] Int. Cl.$^6$ ............... C07C 309/73; C07C 43/205; C07C 39/08
[52] U.S. Cl. ................ 558/58; 549/445; 549/436; 549/434; 549/416; 558/44; 560/254; 568/652; 568/651; 568/649
[58] Field of Search ................ 549/434, 436, 549/445, 416; 558/58, 44; 568/649, 651, 652; 560/254

[56] References Cited

U.S. PATENT DOCUMENTS 5,061,727 10/1991 Bloom et al. .

FOREIGN PATENT DOCUMENTS 2832602 8/1979 Germany .

OTHER PUBLICATIONS

Reiner Luckenback, Beilsteins Handbook of Organic Chemistry, 1981, pp. 7403-7404.
Bloom, J., et al.; (R,R)-5-[2-[[2-(3-Chlorophenyl)-2-hydroxyethyl]-amino]propyl]-1,3-benzodioxole-2,2-dicarboxylate (CL 316,248), A Patent β-Adrenergic Agonist Virtually Specific for β$_3$ Receptors, A Promising Antidiabetic and Antiobesity Agency; J. Med. Chem., vol. 35, No. 16, pp. 3081-3084, (1992).
Conserva et al., Photochemistry, 29(1), 257-260 (1990).
Marques et al., ibid., 30(1), 360-361 (1992).

Primary Examiner—Nicky Chan
Attorney, Agent, or Firm—Cushman Darby & Cushman

[57] ABSTRACT

An (S)-1-phenyl-2-substituted propane derivative shown by the following formula (I)

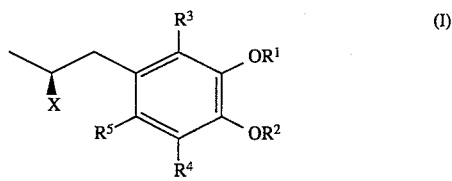

wherein $R^1$ and $R^2$ represent a lower alkyl group, etc., or $R^1$ and $R^2$ may form together an alkylene group, etc.; $R^3$, $R^4$ and $R^5$ represent a hydrogen atom, etc.; and X represents a hydroxyl group which may be protected with a protective group, or a halogen atom etc., can readily be produced (i) by permitting a microorganism belonging to the genus *Torulaspora*, the genus *Candida*, the genus *Pichia* or the like to act on a phenylacetone derivative and asymmetrically reducing the compound, or (ii) by sterically inverting an (R)-enantiomer. (R,R)-1-phenyl-2-[(2-phenyl-1-methylethyl)amino]ethanol derivative having a high optical purity can easily be obtained from the compound of the formula (I). The ethanol derivative is useful as an anti-obesity agent and the like.

8 Claims, No Drawings

OPTICALLY ACTIVE 1-PHENYL-2-SUBSTITUTED PROPANE DERIVATIVES AND METHODS OF PRODUCING THE SAME

FIELD OF THE INVENTION

The present invention relates to an optically active (S)- or (R)-1-phenyl-2-substituted propane derivative which is an important intermediate for synthesis of an (R,R)-1-phenyl-2-[(2-phenyl-1-methylethyl)amino]ethanol derivative, and a method of producing the same. The present invention further relates to a method of producing the ethanol derivative which is useful as a medical compound or an intermediate product thereof.

BACKGROUND OF THE INVENTION

As anti-obesity agents or anti-diabetic agents belonging to a new category of agents without using insulin, 1-phenyl-2-[(2-phenyl-1-methylethyl)amino]ethanol derivatives are noted since the derivatives act selectively on a $\beta_3$-receptor in vivo, thus having extremely low side effects. Pharmacological studies on the 1-phenyl-2-[(2-phenyl-1-methylethyl)amino]ethanol derivatives have revealed that the $\beta_3$-action substantially depends on (R, R)-enantiomers thereof (see J. Med. Chem., 35, 3081 (1992), and U.S. Pat. No. 5,061,727). For example, the above-mentioned U.S. Patent discloses that an (R, R) -5-[2-[[2-(3-chlorophenyl)-2-hydroxyethyl]amino]propyl]-1,3-benzodioxole-2,2-dicarboxylic acid disodium salt has a higher activity than the corresponding (S, S)-enantiomer by a factor of 47.

For the production of an optically active 1-phenyl-2-[(2-phenyl-1-methylethyl)amino]ethanol derivative, there is known an optical resolution of a racemic form or a racemate, or an asymmetric synthesis.

For example, the above mentioned U.S. Pat. No. 5,061,727 discloses a method of producing an (R, R)-1-phenyl-2-[(2-phenyl-1-methylethyl)amino]ethanol derivative which comprises (1) allowing a racemic 2-amino-1-phenylethanol derivative to react with a phenylacetone derivative and sodium cyanoborohydride to produce a mixture of four species of optical isomers of a 1-phenyl-2-[(2-phenyl-1-methylethyl)amino]ethanol derivative, (2) isolating and removing an (R,S)-isomer and an (S,R)-isomer from the mixture, and (3) optically resoluting an (R,R)-isomer and an (S,S)-isomer by a diastereomer method. According to this method, however, it is necessary to isolate and purify only the (R,R)-isomer from the mixture of the four species of optical isomers, therefore, the processes are complicated and the yield is decreased. Further, since large quantities of raw materials are required, the method is also disadvantageous in economical factor.

The U.S. Patent and the Journal of Medicinal Chemistry as mentioned above disclose a method allowing an (R)-3-chlorostyrene oxide derivative to react with an (R)-1-methyl-2-phenylethylamine derivative. The (R)-1-methyl-2-phenylethylamine derivative used as a raw material or reactant in the method, however, has a strong antihypnotic or arousal action and it requires a particular attention when handled, therefore is not suited for a use in commercial production. Further, a lot of steps or processes are required to obtain the above-mentioned two reactants. For instance, the (R)-3-chlorostyrene oxide derivative is prepared from an acetophenone derivative through three steps, that is, chlorination, asymmetric reduction and epoxidation, and the (R)-1-methyl-2-phenylethylamine derivative is prepared from L-DOPA through six steps, namely, introduction of a protective group into an amino group, esterification, reduction of the resulting ester, converting a hydroxyl group to a mesyloxy group, removal of the protective group and reduction.

SUMMARY OF THE INVENTION

Accordingly, it is an object of the present invention to provide an optically active compound which is useful for the efficient production of an (R,R)-1-phenyl-2-[(2-phenyl-1-methylethyl)amino]ethanol derivative with a good yield.

It is another object of the invention to provide a process for producing the compound efficiently with high yield and optical purity.

Still another object of the invention is to provide an optically active compound which is useful for the production of the derivative and is available and easy to handle or treat.

It is a further object of the present invention to provide a process for producing an (R,R)-1-phenyl-2-[(2-phenyl-1-methylethyl)amino]ethanol derivative having a higher optical purity efficiently with a high yield.

A yet further object of the present invention is to provide an optically active (R)-enantiomer which is suitable for the production of the optically active compound being useful for producing the (R, R)-1-phenyl-2-[(2-phenyl-1-methylethyl)amino]ethanol derivative, and a process for producing the same.

The present invention further relates to a process for asymmetrically reducing an phenylacetone derivative to the optically active compound, and to a use of a microorganism in production of the optically active intermediate.

After much studies and efforts to accomplish the above mentioned objects, the present inventors found that an optically active (S)- or (R)-1-phenyl-2-substituted propane derivative having a high optical purity can be obtained with a high yield by permitting a microorganism capable of asymmetrically reducing a phenylacetone derivative to act on the phenylacetone derivative, and that an optically active (R,R)-1-phenyl-2-[(2-phenyl-1-methylethyl)amino]ethanol derivative can easily or readily be produced from the (S)- or (R)-1-phenyl-2-substituted propane derivative with high yield and selectivity. The present invention has been accomplished based on the above findings.

Thus, the present invention provides an (S)-1-phenyl-2-substituted propane derivative shown by the following formula (I)

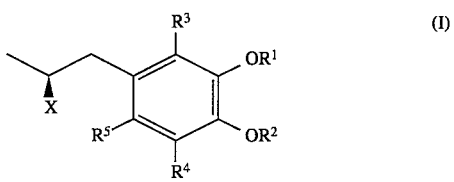

wherein $R^1$ and $R^2$ represent (a) the same or different, a hydrogen atom or a protective group for hydroxyl group, or (b) $R^1$ and $R^2$ may form an optionally substituted ring with the adjacent oxygen atoms; $R^3$, $R^4$ and $R^5$ independently represent a hydrogen atom, a lower alkyl group, a lower haloalkyl group, a lower alkoxy group, a nitro group or a halogen atom; and X represent a hydroxyl group which may be protected with a protective group, an optionally substituted alkylsulfonyloxy group, an optionally substituted arylsulfonyloxy group or a halogen atom.

The (S)-1-phenyl-2-substituted propane derivative of the general formula (I) may be produced by, for example, a process which comprises:

permitting a microorganism which is capable of asymmetrically reducing a phenylacetone derivative shown by the following formula (II)

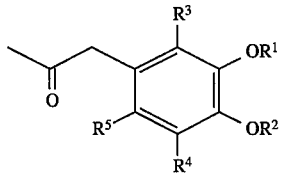
(II)

wherein $R^1$, $R^2$, $R^3$, $R^4$ and $R^5$ have the same meanings as defined above, to a corresponding (S)-1-phenylpropanol derivative shown by the following formula (III)

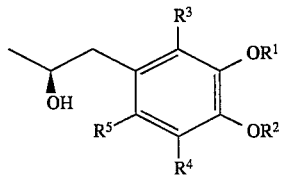
(III)

wherein $R^1$, $R^2$, $R^3$, $R^4$ and $R^5$ have the same meanings as defined above, or a preparation thereof to act on the phenylacetone derivative, and harvesting or recovering the product (S)-1-phenylpropanol derivative.

Further, the (S)-1-phenyl-2-substituted propane derivative of the general formula (I) may also be obtained by, for instance, allowing a sulfonylating agent or a halogenating agent to react with the (S)-1-phenylpropanol derivative of the general formula (III).

The (S)-1-phenyl-2-substituted propane derivative of the general formula (I) is useful for production of an (R,R)-1-phenyl-2-[(2-phenyl-1-methylethyl) amino]ethanol derivative shown by the following formula (VI)

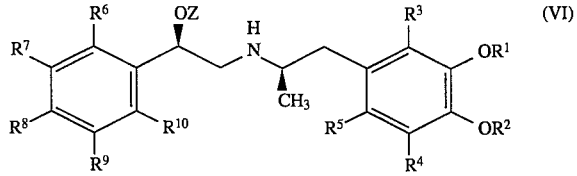
(VI)

wherein $R^1$, $R^2$, $R^3$, $R^4$, $R^5$, $R^6$, $R^7$, $R^8$, $R^9$, $R^{10}$ and Z have the same meanings as defined above, or a salt thereof.

The present invention further provides an (R)-1-phenyl-2-substituted propane derivative shown by the general formula (VII)

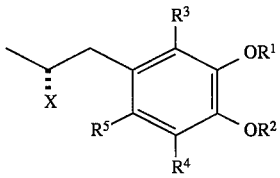
(VII)

wherein $R^1$, $R^2$, $R^3$, $R^4$, $R^5$ and X have the same meanings as defined above.

The (R)-1-phenyl-2-substituted propane derivative of the general formula (VII) may be produced by, for instance, utilizing a function of a microorganism which is capable of asymmetrically reducing the phenylacetone derivative of the general formula (II) to produce the corresponding (R)-1-phenyl-2-propanol derivative shown by the following formula (VII')

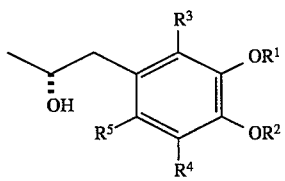
(VII')

wherein $R^1$, $R^2$, $R^3$, $R^4$ and $R^5$ have the same meanings as defined above, or a preparation thereof.

The (R)-1-phenyl-2-substituted propane derivative of the general formula (VII) may, for instance, be sterically inverted to the (S)-1-phenyl-2-substituted propane derivative of the general formula (I) with the use of a nucleophilic reagent.

The present invention still further discloses a process for asymmetrically reducing the phenylacetone derivative of the general formula (II) to the corresponding (S)- or (R)-1-phenyl propane derivative, and a use of a microorganism capable of asymmetrically reducing the phenylacetone derivative of the general formula (II), or a preparation thereof for the production of the corresponding (S)- or (R)-1-phenyl-2-substituted propane derivative.

DETAILED DESCRIPTION OF THE INVENTION

The (S)-1-phenyl-2-substituted propane derivatives shown by the general formula (I) are particularly useful as intermediates for synthesis of the (R,R)-1-phenyl-2-[(2-phenyl-1-methylethyl)amino]ethanol derivatives which are usable as medicinal compounds or drugs, or intermediate materials thereof.

As the protective group for hydroxyl group in $R^1$ and $R^2$, there may be mentioned protective groups for a hydroxyl group generally employed in the field of organic synthesis. Such protective groups include, for example, (A) a group which forms an ether bond with an oxygen atom, (B) a group which forms an ester bond with an oxygen atom, (C) a group which forms a carbonate with an oxygen atom and (D) a group which forms a sulfonic acid ester with an oxygen atom.

Examples of the group (A) which forms an ether bond with an oxygen atom include (1) an optionally substituted lower alkyl group, (2) an optionally substituted allyl group, (3) an optionally substituted cycloalkyl group, (4) an optionally substituted heterocyclic group, (5) an optionally substituted aralkyl group and (6) an optionally substituted silyl group.

The optionally substituted lower alkyl group (1) includes, for example, (a) an optionally substituted alkyl group having 1 to 4 carbon atoms such as methyl, ethyl, n-propyl, i-propyl, n-butyl, i-butyl, s-butyl and t-butyl groups. The substituents for the $C_{1-4}$ alkyl group include, for example, a $C_{1-4}$ alkoxy group, a $C_{1-4}$ alkoxy-$C_{1-4}$ alkoxy group, a $C_{7-20}$ aralkyloxy group, a benzoyl group, a $C_{1-4}$ alkylthio group and a halogen atom and so on. Examples of such substituted $C_{1-4}$ alkyl group include (b) a $C_{1-4}$ alkoxy-$C_{1-4}$ alkyl group such as methoxymethyl, ethoxymethyl, t-butoxymethyl, 1-methoxyethyl, 1-ethoxyethyl, 2-methoxyethyl (especially a $C_{1-4}$ alkoxy-$C_{1-2}$ alkyl group); (c) an $C_{1-4}$ alkoxy-$C_{1-4}$ alkoxy-$C_{1-4}$ alkyl group such as 2-methoxyethoxymethyl, 2-ethoxymethoxymethyl and the like (specifically a $C_{1-4}$ alkoxy-$C_{1-4}$ alkoxy-$C_{1-2}$ alkyl group); (d) a $C_{7-20}$ aralkyloxy-$C_{1-4}$ alkyl group such as benzyloxymethyl (especially, a $C_{7-20}$ aralkyloxymethyl group); (e) a phenacyl group; (f) a $C_{1-4}$ alkylthio-$C_{1-4}$ alkyl group such as methylthiomethyl, ethylthiomethyl (specifically a $C_{1-4}$ alkylthiomethyl group); and (g) a $C_{1-4}$ haloalkyl group having one or more of halogen atoms such as trichloromethyl, trifluoromethyl, 2,2,2-trichloroethyl, 2,2,2-trifluoroethyl and the like.

The optionally substituted allyl group (2) includes, for instance, an allyl group. Examples of the optionally substituted cycloalkyl group (3) include a cycloalkyl group having 3 to 10 carbon atoms such as cyclopropyl, cyclopentyl, cyclohexyl, cycloheptyl, cyclooctyl, cyclononyl and cyclodecyl.

As the optionally substituted heterocyclic group (4), there may be mentioned, for example, an optionally substituted 5- to 6-membered heterocyclic group having an oxygen atom or a sulfur atom as a hetero atom. The optionally substituted heterocyclic group may frequently be a perhydroheterocyclic group. The 5- to 6-membered heterocyclic group includes, for instance, tetrahydrofuranyl, tetrahydrothiofuranyl, tetrahydropyranyl and tetrahydrothiopyranyl. Examples of the substituent for the heterocyclic group include a halogen atom, a $C_{1-4}$ alkyl group, a $C_{1-4}$ alkoxy group such as methoxy, ethoxy, propoxy, isopropoxy, butoxy, isobutoxy, s-butoxy and t-butoxy, and others as mentioned above. Practical examples of the optionally substituted heterocyclic group include an optionally substituted tetrahydropyranyl group (e.g. tetrahydropyranyl, 3-bromotetrahydropyranyl, 4-methoxytetrahydropyranyl, etc.), an optionally substituted tetrahydrothiopyranyl group (for example, tetrahydrothiopyranyl, 3-bromotetrahydrothiopyranyl, 4-methoxytetrahydrothiopyranyl, etc.), an optionally substituted tetrahydrofuranyl group (for instance, tetrahydrofuranyl, etc.), and an optionally substituted tetrahydrothiofuranyl group (e.g. tetrahydrothiofuranyl).

Examples of the optionally substituted aralkyl group (5) include an optionally substituted aralkyl group having 7 to 20 carbon atoms (e.g. benzyl, etc.). The substituent for the aralkyl group includes, for instance, a $C_{1-4}$ alkyl group; a halogen atom; a nitro group; a $C_{1-4}$ alkoxy group; a $C_{6-12}$ aryl group such as phenyl. Examples of such substituent may be referred to those in above group (4). Typical examples of the optionally substituted aralkyl group include an optionally substituted $C_{7-20}$ aralkyl group such as benzyl, o-chlorobenzyl, o-nitrobenzyl, p-chlorobenzyl, p-methoxybenzyl, p-methylbenzyl, p-nitrobenzyl, 2,6-dichlorobenzyl, diphenylmethyl, trityl and the like.

The substituent for the silyl group (6) includes a $C_{7-20}$ aralkyl group such as benzyl group and substituents as mentioned in the aralkyl group (5). Examples of the optionally substituted silyl group (6) include trimethylsilyl, triethylsilyl, t-butyldimethylsilyl, tribenzylsilyl, triphenylsilyl and so on.

As the group (B) which forms an ester bond with an oxygen atom, there may be mentioned, for example, an optionally substituted acyl group including (1) an optionally substituted acyl group having 1 to 6 carbon atoms such as formyl, acetyl, chloroacetyl, trifluoroacetyl, propionyl, isopropionyl, butyryl, isobutyryl, valeryl, isovaleryl, pivaloyl and the like; (2) an optionally substituted $C_{7-16}$ acyl group having an aromatic ring such as benzoyl, p-phenylbenzoyl, toluoyl, naphthoyl and others; (3) an optionally substituted acyl group having a heterocyclic ring such as furoyl, thenoyl, nicotinoyl and isonicotinoyl groups.

The group (C) which forms a carbonate with an oxygen atom includes, for instance, (1) an optionally substituted $C_{2-5}$ alkoxycarbonyl group such as methoxycarbonyl, ethoxycarbonyl, propoxycarbonyl, isopropoxycarbonyl, butoxycarbonyl, isobutoxycarbonyl, s-butoxycarbonyl and t-butoxycarbonyl; (2) an optionally substituted $C_{8-20}$ aralkyloxycarbonyl group such as benzyloxycarbonyl, p-methoxybenzyloxycarbonyl, p-methylbenzyloxycarbonyl, p-chlorobenzyloxycarbonyl, onitrobenzyloxycarbonyl, etc.; (3) an optionally substituted $C_{7-20}$ aryloxycarbonyl group such as phenoxycarbonyl, 4-methylphenyloxycarbonyl, 4-nitrophenyloxycarbonyl, 4-chlorophenyloxycarbonyl, naphthyloxycarbonyl and so on.

Examples of the group (D) which forms a sulfonic acid ester with an oxygen atom include (1) an optionally substituted alkylsulfonyl group such as an optionally substituted $C_{1-4}$ alkylsulfonyl group (e.g. methanesulfonyl, ethanesulfonyl, trichloromethanesulfonyl, trifluoromethanesulfonyl, etc.); (2) an optionally substituted arylsulfonyl group including an optionally substituted $C_{6-20}$ arylsulfonyl group such as benzenesulfonyl, m-nitrobenzenesulfonyl, p-nitrobenzenesulfonyl, p-chlorobenzenesulfonyl, p-bromobenzenesulfonyl, p-toluenesulfonyl, naphthalenesulfonyl and others.

Preferred examples of $R^1$ and $R^2$ exemplified above include (i) a hydrogen atom; (ii) among the protective groups for hydroxyl group, (A) a group which forms an ether bond with an oxygen atom, specifically, an optionally substituted $C_{1-4}$ alkyl group and an optionally substituted $C_{7-20}$ aralkyl group, and more specifically a $C_{1-4}$ alkyl group, and (B) a group which forms an ester bond with an oxygen atom, especially a $C_{1-6}$ acyl group (e.g. acetyl, etc.).

Where $R^1$ and $R^2$, in incorporation, form a ring together with the adjacent oxygen atoms, the ring may for example be a 5- to 10-membered ring, preferably a 5- to 8-membered ring and more preferably a 5- or 6-membered ring. Such $R^1$ and $R^2$ includes, for instance, an optionally substituted alkylene group, a carbonyl group, a thiocarbonyl group and others.

As the alkylene group, there may be mentioned, for instance, an alkylene group having 1 to 4 carbon atoms such as methylene, ethylene, trimethylene and the like. Preferred alkylene group includes a methylene group.

The optionally substituted methylene group includes, for example, a group shown by the following formula (IX)

(IX)

wherein $R^a$ and $R^b$ represent, (i) the same or different, a hydrogen atom, a $C_{1-4}$ alkyl group, a $C_{1-4}$ haloalkyl group, an optionally substituted $C_{6-20}$ aryl group, a $C_{1-4}$ alkoxy group, an optionally substituted amino group, a carboxyl group or a salt thereof, an optionally substituted alkoxycarbonyl group, a hydroxymethyl group or an optionally substituted alkoxymethyl group, or (ii) $R^a$ and $R^b$ may form a $C_{5-7}$ cycloalkyl group together with the adjacent carbon atom.

The $C_{1-4}$ alkyl group, the $C_{1-4}$ haloalkyl group and the $C_{1-4}$ alkoxy group in $R^a$ and $R^b$ include those exemplified in $R^1$ and $R^2$. The optionally substituted $C_{6-20}$ aryl group in $R^a$ and $R^b$ includes, for instance, phenyl, 4-methoxyphenyl, 2-nitrophenyl and others. As the substituted amino group, there may be mentioned, for example, a mono- or di-$C_{1-4}$ alkylamino group such as methylamino, dimethylamino, ethylamino, diethylamino and others.

As the salt of the carboxyl group represented by $R^a$ and $R^b$, any salt can be employed. A salt which is pharmacologically acceptable may frequently be used. Examples of such salt include a salt with an inorganic base such as an alkali metal salt (e.g. a sodium salt or a potassium salt), an alkaline earth metal salt (for instance, a magnesium salt, a calcium salt or a barium salt), a metal salt (e.g. a zinc salt or an aluminum salt) and an ammonium salt; a salt with an organic base such as a salt with pyridine, a tri-$C_{1-3}$ alkylamine (e.g. trimethylamine, triethylamine, etc.) and so on.

The optionally substituted alkoxycarbonyl group in $R^a$ and $R^b$ includes, for instance, an optionally substituted $C_{2-5}$ alkoxycarbonyl group as mentioned in $R^1$ and $R^2$.

As examples of the optionally substituted alkoxymethyl group in $R^a$ and $R^b$, there may be mentioned an optionally substituted a $C_{1-4}$ alkoxy-methyl group which may be substituted on the alkyl with a substituent. Such substituent for the alkoxymethyl group include, for example, a carboxyl group, a $C_{2-5}$ alkoxycarbonyl group, a hydroxyl group and a $C_{1-4}$ alkoxy group. The $C_{2-5}$ alkoxycarbonyl group and the $C_{1-4}$ alkoxy group can be referred to the groups as mentioned in $R^1$ and $R^2$. Typical examples of the optionally substituted alkoxymethyl group include (a) a $C_{1-4}$ alkoxymethyl group such as methoxymethyl, ethoxymethyl, propoxymethyl, isopropoxymethyl, butoxyemthyl, isobutoxymethyl, s-butoxymethyl and t-butoxymethyl; (b) a carboxy-$C_{1-4}$ alkoxy-methyl group such as carboxymethoxymethyl, carboxyethoxymethyl, carboxypropoxymethyl, carboxybutoxymethyl, etc.; (c) a $C_{2-5}$ alkoxycarbonyl-$C_{1-4}$ alkoxy-methyl group such as methoxycarbonylmethoxymethyl, ethoxycarbonylmethxoymethyl, isopropoxycarbonylmethoxymethyl, 2-butoxycarbonylethoxymethyl and others; (d) a hydroxy-$C_{1-4}$ alkoxy-methyl group such as 2-hydroxyethoxymethyl, 3-hydroxypropoxymethyl and the like; (e) a $C_{1-4}$ alkoxy-$C_{1-4}$ alkoxy-methyl group such as 2-methoxyethoxymethyl, 2-ethoxyethoxymethyl, 3-methoxypropoxymethyl and so on.

The $C_{5-7}$ cycloalkyl group includes cyclopentyl, cyclohexyl and cycloheptyl groups.

As preferred examples of the optionally substituted methylene group shown by the formula (IX), there may be mentioned, for instance, (a) the group of the formula (IX) wherein $R^a$ and $R^b$ are, the same or different, a hydrogen atom, a $C_{1-4}$ alkyl group or a $C_{5-7}$ cycloalkyl group formed with $R^a$, $R^b$ and the adjacent carbon atom (e.g. a methylene group, a $C_{2-4}$ alkylidene group such as an ethylidene group and an isopropylidene group; a $C_{5-7}$ cycloalkylidene group such as a cyclopentylidene and a cyclohexylidene, and so on); (b) the group of the formula (IX) where $R^a$ and $R^b$ are respectively a carboxyl group or a salt thereof, an optionally substituted alkoxycarbonyl group, a hydroxymethyl group or an optionally substituted alkoxymethyl group. Specifically preferred is the group of the formula (IX) where $R^a$ and $R^b$ are, the same or different, a carboxyl group or a salt thereof, or a $C_{2-5}$ alkoxycarbonyl group.

Practically preferred examples of $R^1$ and $R^2$ include, a hydrogen atom, a $C_{1-4}$ alkyl group (particularly a methyl group), the optionally substituted methylene group of the formula (IX) formed by incorporation of $R^1$ and $R^2$ where $R^a$ and $R^b$ are respectively a carboxyl group or a salt thereof, or a $C_{2-5}$ alkoxycarbonyl group.

Examples of the lower alkyl group in $R^3$, $R^4$ and $R^5$ include a $C_{1-4}$ alkyl group as exemplified in $R^1$ and $R^2$.

The lower haloalkyl group in $R^3$, $R^4$ and $R^5$ includes, for instance, a haloalkyl group having 1 to 4 carbon atoms and one or more of halogen atoms such as chloromethyl, 2-chloroethyl, 4-chlorobutyl, trichloromethyl, trifluoromethyl and 1,1,2,2,2-pentafluoroethyl groups. As examples of the lower alkoxy group and the halogen atom, there may be mentioned a $C_{1-4}$ alkoxy group and halogen atoms as mentioned in the explanation of $R^1$ and $R^2$.

Preferred substituents of $R^3$, $R^4$ and $R^5$ include, for example, a hydrogen atom and a lower alkyl group, especially a hydrogen atom.

The protective group of hydroxyl group in X as mentioned above includes an protective group for an alcoholic hydroxyl group usually or generally used in the field of organic synthesis. Examples of such protective group include the protective groups (A) to (C) as mentioned in the protective groups for a hydroxyl group in $R^1$ and $R^2$.

The halogen atom in X includes the halogen atoms mentioned above.

Examples of the optionally substituted alkylsulfonyloxy group in X include an optionally substituted $C_{1-4}$ alkylsulfonyloxy group such as methanesulfonyloxy, ethanesulfonyloxy, trichloromethanesulfonyloxy and trifluoromethanesulfonyloxy groups.

As examples of the optionally substituted arylsulfonyloxy group, there may be mentioned an optionally substituted $C_{6-20}$ arylsulfonyloxy group such as benzensulfonyloxy, m-nitrobenzenesulfonyloxy, p-nitrobenzenesulfonyloxy, p-chlorobenzenesulfonyloxy, p-bromobenzenesulfonyloxy, p-toluenesulfonyloxy, naphthalenesulfonyloxy and others.

Typical examples of X include a hydroxyl group and a group which plays as a leaving group in a replacement reaction such as an optionally substituted $C_{1-4}$ alkylsulfonyloxy group, an optionally substituted $C_{6-20}$ arylsulfonyloxy group, a halogen atom and the like. Particularly, a hydroxyl group; an optionally substituted alkylsulfonyloxy group having 1 or 2 carbon atoms such as methanesulfonyloxy group; an optionally substituted arylsulfonyloxy group having 6 to 15 carbon atoms such as p-toluenesulfonyloxy group; chlorine atom, bromine atom and iodine atom are preferable.

In the (S)-1-phenyl-2-substituted propane derivative of the general formula (I), preferred examples include compounds where $R^1$ and $R^2$ are, the same or different, (i) a hydrogen atom, a $C_{1-4}$ alkyl group (specifically a methyl group) or (ii) $R^1$ and $R^2$ incorporatively form an optionally substituted methylene group of the formula (IX) wherein $R^a$ and $R^b$ are respectively a carboxyl group or a salt thereof, or a $C_{2-5}$ alkoxycarbonyl group; $R^3$, $R^4$, and $R^5$ are independently a hydrogen atom or a $C_{1-4}$ alkyl group; and X is a hydroxyl group, a $C_{1-2}$ alkylsulfonyloxy group, a $C_{6-15}$ arylsulfonyloxy group or a halogen atom.

Practical examples of the (S)-1-phenyl-2-substituted propane derivative shown by the general formula (I) include (1) an (S)-1-(3,4-dihydroxyphenyl)-2-substituted propane derivative, (2) an (S)-1-(3,4-di-$C_{1-4}$ alkoxyphenyl)-2-substituted propane derivative, (3) an (S)-1-(2,2-di-$C_{1-4}$ alkyl-1,3-benzodioxol-5-yl)-2-substituted propane derivative, (4) an (S)-1-[2,2-bis($C_{2-5}$-alkoxycarbonyl)-1,3-benzodioxol-5-yl]-2-substituted propane derivative and (5) an (S)-1(2,2-dicarboxy-1,3-benzodioxol-5-yl ) -2-substituted propane derivative.

As the (S)-1-(3,4-dihydroxyphenyl)-2-substituted propane derivative (1), there may be mentioned, for instance, (S)-1-(3,4-dihydroxyphenyl)-2-propanol, (S)-[2(3,4-dihydroxyphenyl)-1-methylethyl p-toluenesulfonate], (S)-[2-(3,4-dihydroxyphenyl)-1-methylethyl methanesulfonate], (S)-2-chloro-1-(3,4-dihydroxyphenyl)propane, (S)-2-bromo-1-(3,4-dihydroxyphenyl)propane and the like.

Examples of the (S)-1-(3,4-di-$C_{1-4}$ alkoxyphenyl)-2-substituted propane derivative (2) include (S)-1-(3,4-dimethoxyphenyl)-2-propanol, (S)-[2(3,4-dimethoxyphenyl) -1-methylethyl p-toluenesulfonate], (S)-[2-(3,4-dimethoxyphenyl) 1-methylethyl methanesulfonate], (S) -2-chloro-1-(3,4-dimethoxyphenyl)propane, (S)-2-bromo-1-(3,4-dimethoxyphenyl)propane and so on.

The (S)-1-(2,2-di-$C_{1-4}$ alkyl-1,3-benzodioxol- 5-yl)-2-substituted propane derivative (3) includes, for example, (S)-1-(2,2-dimethyl-1,3-benzodioxol-5-yl) -2-propanol, (S)-[1-methyl-2-(2,2-dimethyl-1,3-benzodioxol-5-yl)ethyl p-toluenesulfonate], (S)-[1-methyl-2-(2,2-dimethyl-1,3-benzodioxol-5-yl)ethyl methanesulfonate], (S)-2-chloro-1-(2,2-dimethyl-1,3-benzodioxol-5-yl)propane, (S)-2-bromo-1-(2,2-dimethyl-1,3-benzodioxol-5-yl)propane, etc.

As examples of the (S)-1-[2,2-bis ($C_{2-5}$-alkoxycarbonyl)-1,3-benzodioxol-5-yl]-2-substituted propane derivative (4), there may be mentioned (S)-[dimethyl 5(2-hydroxypropyl)-1,3-benzodioxole-2,2-dicarboxylate], (S)-[diethyl 5-(2-hydroxypropyl)-1,3-benzodioxole-2,2-dicarboxylate], (S)-[dimethyl 5-[2-(p-toluenesulfonyloxy)propyl]-1,3-benzodioxole-2,2-dicarboxylate], (S)-[diethyl 5-[2-(p-toluenesulfonyloxy)propyl]-1,3-benzodioxole-2,2-dicarboxylate], (S)-[dimethyl 5-[2-(methanesulfonyloxy)propyl]-1,3-benzodioxole-2,2-dicarboxylate], (S)-[diethyl 5-[2-(methanesulfonyloxy)propyl]-1,3-benzodioxole-2,2-dicarboxylate], (S)-[dimethyl 5-(2-chloropropyl)-1,3-benzodioxole-2,2-dicarboxylate], (S)-[diethyl 5-(2-chloropropyl)-1,3-benzodioxole-2,2-dicarboxylate], (S)-[dimethyl 5-(2-bromopropyl)-1,3-benzodioxole-2,2-dicarboxylate], (S)-[diethyl 5-(2-bromopropyl)-1,3-benzodioxole-2,2-dicarboxylate] and the like.

Examples of the (S)-1-(2,2-dicarboxy-1,3-benzodioxol-5-yl)-2-substituted propane derivative (5) include (S)-[disodium 5-[2-(hydroxypropyl)-1,3-benzodioxole-2,2-dicarboxylate], (S)-[disodium 5- [2-(p-toluenesulfonyloxy)propyl]-1,3-benzodioxole-2,2-dicarboxylate], (S)-[disodium 5-[2-(methanesulfonyloxy)propyl]-1,3-benzodixole-2,2-dicarboxylate], (S)-[disodium 5-(2-chloropropyl)-1,3-benzodioxole-2,2-dicarboxylate], (S)-[disodium 5-(2-bromopropyl)-1,3-benzodioxole-2,2-dicarboxylate] and others.

The (S)-1-phenyl-2-substituted propane derivative of the general formula (I) can be prepared by a variety of methods, for instance, by a chemical reaction, and can advantageously be prepared by utilizing an action of a microorganism or a preparation thereof.

Among the (S)-1-phenyl-2-substituted propane derivatives shown by the general formula (I) , (a) the compound wherein X is a hydroxyl group, that is, (S)-1-phenyl-2-propanol derivative shown by the general formula (III) can easily be obtained by asymmetrical reduction of the phenylacetone derivative shown by the general formula (II), (i) with the use of a microorganism or a preparation thereof, or (ii) in a chemical method, and harvesting or recovering the product (S)-1-phenyl-2-propanol derivative.

In the method (i), the (S)-1-phenyl-2-substituted propane derivative of the general formula (I) can be obtained by permitting a microorganism or a preparation thereof to act on the phenylacetone derivative of the general formula (II) and harvesting or recovering the objective product.

The phenylacetone derivative of the general formula (II) used as a raw material can easily be obtained by a conventional manner, for example, dry distillation of a mixture of an acetic acid salt such as an acetic acid salt with an alkaline earth metal (e.g. calcium acetate and barium acetate) and a phenylacetic acid salt corresponding to the compound of the general formula (II) such as a phenyl acetic acid salt with an alkaline earth metal salt (for instance, calcium phenylacetate, barium phenylacetate, etc.) or others.

The microorganisms to be employed in accordance with the method may be any strain of microorganism that is capable of asymmetrically reducing a phenylacetone derivative shown by the general formula (II) to produce the optically active (S)-1-phenyl-2-substituted propane derivative shown by the general formula (III).

Examples of such microorganisms a strain of microorganism belonging to the genus *Sphingobacterium*, the genus *Aeromonas*, the genus *Agrobacterium*, the genus *Aureobacterium*, the genus *Bacillus*, the genus *Cellulomonas*, the genus *Chromobacterium*, the genus *Corynebacterium*, the genus *Gluconobacter*, the genus *Jensenia*, the genus *Comamonas*, the genus *Pseudomonas*, the genus *Alternaria*, the genus *Areanita*, the genus *Aspergillus*, the genus *Cochliobolus*, the genus *Corynespora*, the genus *Dactylium*, the genus *Drechslera*, the genus *Echinopodospora*, the genus *Gelasinospora*, the genus *Gonatobotryum*, the genus *Helminthosporium*, the genus *Mortierella*, the genus *Paecilomyces*, the genus *Phialophora*, the genus *Phytophthora*, the genus *Podospora*, the genus *Rhizomucor*, the genus *Septoria*, the genus *Sporormiella*, the genus *Stemphylium*, the genus *Talaromyces*, the genus *Torula*, the genus *Ustilago*, the genus *Westerdykella*, the genus *Ambrosiozyma*, the genus *Dekkera*, the genus *Candida*, the genus *Clavispora*, the genus *Cryptococcus*, the genus *Debaryomyces*, the genus *Galactomyces*, the genus *Filobasidium*, the genus *Geotrichum*, the genus *Hansenula*, the genus *Issatchenkia*, the genus *Kloeckera*, the genus *Kluyveromyces*, the genus *Leucosporidium*, the genus *Lodderomyces*, the genus *Metschnikowia*, the genus *Myxozyma*, the genus *Oosporidium*, the genus *Pachysolen*, the genus *Pichia*, the genus *Malassezia*, the genus *Rhodosporidium*, the genus *Kondoa*, the genus *Rhodotorula*, the genus *Saccharomyces*, the genus *Octosporomyces*, the genus *Sporidiobolus*, the genus *Sporobolomyces*, the genus *Sporopachydermia*, the genus *Sterigmatomyces*, the genus *Torulaspora*, the genus *Torulopsis*, the genus *Trigonopsis*, the genus *Wickerhamia*, the genus *Wingea*, the genus *Zygoascus*, the genus *Zygosaccharomyces*, the genus *Zygozyma* and others.

(1) The strain of microorganism belonging to the genus *Sphingobacterium* includes *Sphingobacterium* sp. IFO 13310, etc.

(2) The strain of microorganism belonging to the genus *Aeromonas* includes *Aeromonas hydrophila* subsp. proteolytiga IFO 13287, etc.

(3) The strain of microorganism belonging to the genus *Agrobacterium* includes *Agrobacterium radiobacter* IFO 12664, etc.

(4) The strain of microorganism belonging to the genus *Aureobacterium* includes *Aureobacterium testaceum* IFO 12675, etc.

(5) The strain of microorganism belonging to the genus *Bacillus* includes *Bacillus cereus* AHU 1355, etc.

(6) The strain of microorganism belonging to the genus *Cellulomonas* includes *Cellulomonas flavigena* IFO 3754, etc.

(7) The strain of microorganism belonging to the genus *Chromobacterium* includes *Chromobacterium iodinum* IFO 3558, etc.

(8) The strain of microorganism belonging to the genus *Corynebacterium* includes *Corynebacterium aquaticum* IFO 12154, etc.

(9) The strain of microorganism belonging to the genus *Gluconobacter* includes *Gluconobacter oxydans* IFO 3255, etc.

(10) The strain of microorganism belonging to the genus Jensenia includes *Jensenia canicruria* IFO 13914, etc.

(11) The strain of microorganism belonging to the genus Comamonas includes *Comamonas acidovorans* IFO 13582, etc.

(12) The strain of microorganism belonging to the genus Pseudomonas includes *Pseudomonas fluorescens* IFO 3081, *Pseudomonas putida* IFO 3738, etc.

(13) The strain of microorganism belonging to the genus Alternaria includes *Alternaria japonica* IFO 5244, etc.

(14) The strain of microorganism belonging to the genus Amanita includes *Amanita citrina* IFO 8261, etc.

(15) The strain of microorganism belonging to the genus Aspergillus includes *Aspergillus awamori nakazawa* IFO 4033, *Aspergillus ficuum* IFO 4018, *Aspergillus niger* AHU 7105, *Aspergillus niger* IFO 5374, etc.

(16) The strain of microorganism belonging to the genus Cochliobolus includes *Cochliobolus miyabeanus* IFO 6631, etc.

(17) The strain of microorganism belonging to the genus Corynespora includes *Corynespora cassiicola* IFO 6724, etc.

(18) The strain of microorganism belonging to the genus Dactylium includes *Dactylium dendroides* ATCC 46032, etc.

(19) The strain of microorganism belonging to the genus Drechslera includes *Drechslera avenae* IFO 6636, etc.

(20) The strain of microorganism belonging to the genus Echinopodospora includes *Echinopodospora jamaicensis* IFO 9819, etc.

(21) The strain of microorganism belonging to the genus Gelasinospora includes *Gelasinospora cerealis* IFO 6759, etc.

(22), The strain of microorganism belonging to the genus Gonatobotryum includes *Gonatobotryum apiculatum* IFO 9098, etc.

(23) The strain of microorganism belonging to the genus Helminthosporium includes *Helminthosporium sigmoideum* var. *irregulare* IFO 5273, etc.

(24) The strain of microorganism belonging to the genus Mortierella includes *Mortierella isabeilina* IFO 6336, etc.

(25) The strain of microorganism belonging to the genus Paecilomyces includes *Paecilomyces variotii* IFO 4855, etc.

(26) The strain of microorganism belonging to the genus Phialophora includes *Phialophora pedrosoi* IFO 6071, etc.

(27) The strain of microorganism belonging to the genus Phytophthora includes *Phytophthora capsici* IFO 8386, etc.

(28) The strain of microorganism belonging to the genus Podospora includes *Podospora carbonaria* IFO 30294, etc.

(29) The strain of microorganism belonging to the genus Rhizomucor includes *Rhizomucor pusillus* IFO 4578, etc.

(30) The strain of microorganism belonging to the genus Septoria includes *Septoria glycines* IFO 5294, etc.

(31) The strain of microorganism belonging to the genus Sporormielia includes *Sporormielia isomera* IFO 8538, etc.

(32) The strain of microorganism belonging to the genus Stemphylium includes *Stemphylium sarciniforme* IFO 7243, etc.

(33) The strain of microorganism belonging to the genus Talaromyces includes *Talaromyces flavus* var. *flavus* IFO 7231, etc.

(34) The strain of microorganism belonging to the genus Torula includes *Torula jeanselmei* IFO 6857, etc.

(35) The strain of microorganism belonging to the genus Ustilago includes *Ustilago cynodontis* IFO 7530, etc.

(36) The strain of microorganism belonging to the genus Westerdykella includes *Westerdykella multispora* IFO 5813, etc.

(37) The strain of microorganism belonging to the genus Ambrosiozyma includes *Ambrosiozyma cicatricosa* IFO 1846, *Ambrosiozyma monospora* IFO 1965, etc.

(38) The strain of microorganism belonging to the genus Dekkera includes *Dekkera custersianus* IFO 1585, etc.

(39) The strain of microorganism belonging to the genus Candida includes *Candida aaseri* IFO 10104, *Candida atomspherica* IFO 1969, *Candida beechii* IFO 10229, *Candida diversa* IFO 1091, *Candida ergatensis* IFO 10233, *Candida fluviatilis* IFO 10234, *Candida fusiformate* IFO 10225, *Candida glabrata* IFO 0622, *Candida gropengiesseri* IFO 0659, *Candida halonitratophila* IFO 1595, *Candida inconspicua* IFO 0621, *Candida kefyr* DSM 70073, *Candida krusei* DSM 70075, *Candida lambica* DSM 70090, *Candida mogii* IFO 0436, *Candida maltosa* IFO 1978, *Candida melibiosica* IFO 10238, *Candida membranaefaciens* IFO 1246, *Candida oleophila* JCM 2444, *Candida parapsilosis* IFO 1022, *Candida pintolopesii* var. *pintolopesii* IFO 0729, *Candida pseudointermedia* IFO 1693, *Candida catenulata* DSM 70136, *Candida rugosa* IFO 0591, *Candida saitoana* IFO 0768, *Candida sake* IFO 1149, *Candida natalensis* IFO 1981, *Candida salmanticensis* IFO 10242, *Candida santamariae* IFO 1982, *Candida schatavii* IFO 10258, *Candida shehatae* IFO 1983, *Candida silvanorum* IFO 10419, *Candida sorbophila* IFO 1583, *Candida tenuis* IFO 10315, *Candida utilis* IFO 0396, *Candida utilis* IFO 0988, *Candida albicans* IFO 0759, etc.

(40) The strain of microorganism belonging to the genus Clavispora includes *Clavispora lusitaniae* IFO 1019, etc.

(41) The strain of microorganism belonging to the genus Cryptococcus includes *Cryptococcus humicolus* IFO 0760, *Cryptococcus neoformans* IAM 4788, etc.

(42) The strain of microorganism belonging to the genus Debaryomyces includes *Debaryomyces varijiae* DSM 70252, etc.

(43) The strain of microorganism belonging to the genus Galactomyces includes *Galactomyces reessil* IFO 1112, etc.

(44) The strain of microorganism belonging to the genus Filobasidium includes *Filobasidium capsuligenum* IFO 1119, etc.

(45) The strain of microorganism belonging to the genus Geotrichum includes *Geotrichum candidum* IFO 4598, *Geotrichum fermentans* JCM 2467, *Geotrichum fragrans* JCM 2450, etc.

(46) The strain of microorganism belonging to the genus Hansenula includes *Hansenula polymorpha* ATCC 26012, *Hansenula capsulata* DSM 70269, *Hansenula glucozyma* DSM 70271, *Hansenula wickerhamii* DSM 70280, etc.

(47) The strain of microorganism belonging to the genus Issatchenkia includes *Issatchenkia scutulata* var. *scutulata* IFO 10070, etc.

(48) The strain of microorganism belonging to the genus Kloeckera includes *Kloeckera africana* IFO 0869, etc.

(49) The strain of microorganism belonging to the genus Kluyveromyces includes *Kluyveromyces lactis* IFO 0433, *Kluyveromyces marxianus* DSM 70800, *Kluyveromyces polysporus* DSM 70294, etc.

(50) The strain of microorganism belonging to the genus Leucosporidium includes *Leucosporidium scottii* IFO 1924, etc.

(51) The strain of microorganism belonging to the genus *Lodderomyces* includes *Lodderomyces elongisporus* IFO 1676, etc.

(52) The strain of microorganism belonging to the genus *Metschnikowia* includes *Metschnikowia bicuspidata* IFO 1408, *Metschnikowia pulcherrima* DSM 70336, *Metschnikowia reukaufii* DSM 70880, etc.

(53) The strain of microorganism belonging to the genus *Myxozyma* includes *Myxozyma lipomycoides* IFO 10350, etc.

(54) The strain of microorganism belonging to the genus *Oosporidium* includes *Oosporidium margaritiferum* IFO 1208, etc.

(55) The strain of microorganism belonging to the genus *Pachysolen* includes *Pachysolen tannophilus* IFO 1007, etc.

(56) The strain of microorganism belonging to the genus *Pichia* includes *Pichia cellobiosa* DSM 2147, *Pichia farinosa* IFO 1163, *Pichia lindnerii* DSM 70718, *Pichia ohmeri* DSM 70815, *Pichia thermotolerans* IFO 10025, *Pichia pastoris* DSM 70382, *Pichia trehalophila* DSM 70391, *Pichia carsonii* DSM 70392, *Pichia subpelliculosa* IFO 0808, etc.

(57) The strain of microorganism belonging to the genus *Malassezia* includes *Malassezia furfur* IFO 0656, etc.

(58) The strain of microorganism belonging to the genus *Rhodosporidium* includes *Rhodosporidium diobovatum* IFO 1830, *Rhodosporidium toruloides* IFO 1638, etc.

(59) The strain of microorganism belonging to the genus *Kondoa* includes *Kondoa malvinella* IFO 1936, etc.

(60) The strain of microorganism belonging to the genus *Rhodotorula* includes *Rhodotorula glutinis* AHU 3454, *Rhodotorula rubra* IFO 0383, etc.

(61) The strain of microorganism belonging to the genus *Saccharomyces* includes *Saccharomyces rouxii* IAM 0487, etc.

(62) The strain of microorganism belonging to the genus *Octosporomyces* includes *Octosporomyces octosporus* IFO 0353, etc.

(63) The strain of microorganism belonging to the genus *Sporidiobolus* includes *Sporidiobolus johnsonii* IFO 6903, *Sporidiobolus pararoseus* IFO 1104, *Sporidiobolus salmonicolor* IFO 1845, etc.

(64) The strain of microorganism belonging to the genus *Sporobolomyces* includes *Sporobolomyces pararoseus* IFO 1036, etc.

(65) The strain of microorganism belonging to the genus *Sporopachydermia* includes *Sporopachydermia lactativora* IFO 1867, etc.

(66) The strain of microorganism belonging to the genus *Sterigmatomyces* includes *Sterigmatomyces elviae* DSM 70852, etc.

(67) The strain of microorganism belonging to the genus *Torulaspora* includes *Torulaspora delbrueckii* IFO 0381, etc.

(68) The strain of microorganism belonging to the genus *Torulopsis* includes *Torulopsis nemodendra* DSM 70647, etc.

(69) The strain of microorganism belonging to the genus *Trigonopsis* includes *Trigonopsis variabilis* IFO 0755, etc.

(70) The strain of microorganism belonging to the genus *Wickerhamia* includes *Wickerhamia fluorescens* DSM 70715, *Wickerhamiella domercquii* IFO 1857, etc.

(71) The strain of microorganism belonging to the genus *Wingea* includes *Wingea robertsii* IFO 1277, etc.

(72) The strain of microorganism belonging to the genus *Zygoascus* includes *Zygoascus hellenicus* IFO 1575, etc.

(73) The strain of microorganism belonging to the genus *Zygosaccharomyces* includes *Zygosaccharomyces bailii* IFO 0468, *Zygosaccharomyces bisporus* DSM 70415, etc.

(74) The strain of microorganism belonging to the genus *Zygozyma* includes *Zygozyma oligophaga* IFO 10360, etc.

For the purposes of the invention, any of wild strains, mutants and recombinant strains which can be obtained by a genetic engineering technique such as cell fusion or gene manipulation can suitably be used, as far as having the above mentioned ability or capability.

The microorganisms identified hereinabove by IFO numbers are described in the "List of Cultures Ed. 9" published by Institute for Fermentation, Osaka (IFO), Japan and are available from the same Institute. The microorganisms designated by JCM numbers are listed in "Catalogs of Microbial Strains Ed. 5 (1992)" published by the Culture Collection of The Institute of Physical and Chemical Research, Japan and available from the same Culture Collection. The microorganism designated by DSM numbers are listed in "Catalogue of strains (1989)" published by the Deutsch Sammlung von Mikroorganismen (DSM) and are available from the same organization. The yeast identified by ATCC number (*Hansenula polymorpha* ATCC 26012) is listed in "Catalogue of Yeasts, Ed. 18 (1990)" and the filamentous fungus designated by ATCC number (*Dactylium dedroides* ATCC 46032) is listed in "Catalogue of Filamentous fungi, Ed. 18 (1991)" each published by the American Type Culture Collection (ATCC) and are respectively available from the same organization. The microorganisms titled by IAM numbers are available from Institute of Applied Microbiology, Tokyo University, Japan. The microorganisms identified by AHU numbers are available from Faculty of Agriculture, Hokkaido University, Japan.

The medium which is used for growing the strain for use in the invention is not critical in composition only if the selected strain may grow and multiply therein. The medium may frequently be a fluid medium containing sources of carbon and nitrogen and other nutrients. Any carbon source which the strain can utilize may be employed. As the sources of carbon, there may be employed various carbohydrates or saccharides such as glucose, fructose, sucrose, dextrin, starch, etc.; alcohols such as sorbitol, methanol, ethanol, glycerol, etc.; organic acids such as fumaric acid, citric acid, acetic acid, propionic acid, etc. and the corresponding salts; hydrocarbons such as paraffin; and various mixtures thereof. The sources of nitrogen include, for instance, inorganic acid ammonium salts such as ammonium chloride, ammonium sulfate, ammonium phosphate, etc.; organic acid ammonium salts such as ammonium fumarate, ammonium citrate, etc.; inorganic or organic nitrogen-containing materials such as meat extract, yeast extract, malt extract, peptone (polypeptone), corn steep liquor, casein hydrolysate, urea, etc.; and various mixtures thereof.

In the medium, there may be incorporated appropriate amounts of those nutrients which are commonly employed in the cultivation of microorganisms, such as inorganic salts, trace metal salts and vitamins. Where necessary, there may also be incorporated factors which may promote growth of the strain used and/or factors which may augment its ability to produce the object compound of the invention, as well as a buffer substance which may assist in the maintenance of the medium at a given pH.

The cultivation of the microorganism is carried out under conditions optimal for the growth of the particular strain, for example at a medium pH in the range of about 2.0 to 9.5, preferably about 3 to 8, and an incubation temperature in the range of about 20° to 45° C., preferably about 25° to 37° C. The cultivation may be aerobic or anaerobic. The cultivation time is, for example, about 5 to 120 hours, preferably about 12 to 72 hours.

The method of asymmetric reduction is not critical so far as the function of a microorganism or a preparation thereof is acted on the phenylacetone derivative of the general formula (II) to produce the (S)-1-phenyl-2-substituted propane derivative of the general formula (I), and may, for example, be whichever of the following alternatives: (1) a technique adding the phenylacetone derivative to the culture medium where the microorganism is cultivated, (2) a technique adding or mixing the phenylacetone derivative with a culture broth as such to conduct the reaction, (3) a technique which comprises separating the microbial cells from the culture broth, e.g. by centrifugation, resuspending the cells, either as they are or after washing, in a buffer solution, water or the like, and adding the phenylacetone derivative to the resulting cell suspension to treat the mixture therewith.

There are cases in which this reaction proceeds with advantage of a higher yield of the objective optically active compound in the presence of a carbon source such as glucose, sucrose, ethanol, methanol or paraffin which serves as an energy source.

In the reaction, wet viable cells as such can be used, or a treated preparation of cells such as disrupted cells, acetone-treated cells, lyophilized cells can also be employed. These cells or preparation thereof can be employed as immobilized by known techniques such as the polyacrylamide gel method, sulfur-containing polysaccharide gel method (e.g. carrageenin gel method), alginic acid gel method, agar gel method and so on. The enzyme purified from such a cell preparation can also be used. The enzyme can be obtained with the use of known purification processes in a suitable combination.

The corresponding phenylacetone derivative can be used as it is or in the form of a solution, suspension or dispersion containing a suitable solvent. As the solvent, water or an organic solvent which will not interfere with the reaction can be employed. A suspension or a dispersion prepared with a surfactant can also be used when necessary. The phenylacetone derivative may be added in bolus at the beginning of the reaction or in several installments.

The optimal cell concentration of the reaction system can be selected from the range where the yield and the optical purity of the desired optically active compound will not be adversely affected. A typical cell concentration may for example be, on a dry cell basis, about 0.1 to 500 g/liter and preferably about 1 to 300 g/liter. The concentration of the substance phenylacetone derivative is not particularly restricted and is, for example, about 0.01 to 20% by weight and preferably about 0.1 to 10% by weight.

The reaction conditions of the asymmetric reduction can be selected from the ranges that will not detract from the yield of the object compound. For example, the pH of the reaction system can be selected from the range of pH about 2 to 10 and preferably pH about 3 to 8. The reaction temperature is selected from the range of, for example, about 10° to 60° C. and preferably from about 20° to 40° C. and more preferably from about 20° to 35° C. The reaction can be conducted with stirring or under stationary conditions for about 1 to 120 hours.

Thus, when permitting the microorganism or a preparation thereof to act on the phenylacetone derivative, the asymmetric reduction can proceed smoothly or advantageously to produce the corresponding 1-phenyl-2-propanol derivative having an (S)-configuration with a high selectivity.

The (S)-1-phenyl-2-propanol derivative of the general formula (III) produced by the reaction can be recovered or harvested by the separation and purification procedures generally known. For example, the (S)-1-phenyl-2-propanol derivative having a high optical purity can be easily obtained by subjecting the reaction mixture, directly or after separation of the cells, to the conventional purification procedure such as membrane separation, extraction with an organic solvent, crystallization, recrystallization, column chromatography, vacuum concentration and distillation. The optical purity of optically active compound can be measured by high performance liquid chromatography (HPLC) using an optical resolution column.

In the (S)-1-phenyl-2-substituted propane derivatives shown by the general formula (I), (b) the compound wherein X is an optionally substituted alkylsulfonyloxy group, an optionally substituted arylsulfonyloxy group or a halogen atom, that is a compound shown by the general formula (IV), can easily or readily be obtained from the compound of the formula (III) by selecting an reagent, for example a sulfonylating agent or a halogenating agent, a catalyst and reaction conditions from the range where the reaction proceeds with retention in stereochemistry. Such reaction is illustrated, for instance, by the following scheme:

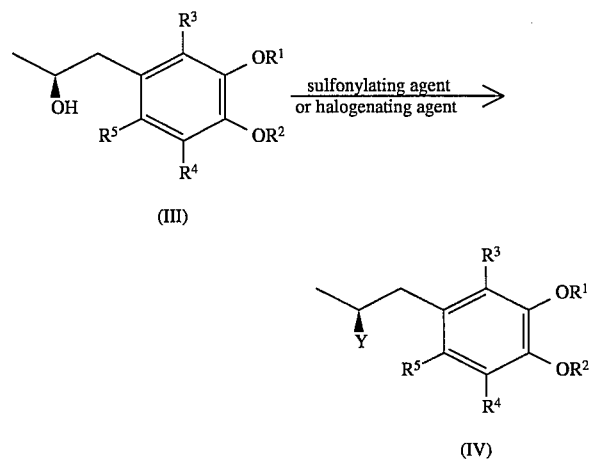

in the general formula (IV), $R^1$, $R^2$, $R^3$, $R^4$ and $R^5$ have the same meanings as defined above; and Y represents an optionally substituted alkylsulfonyloxy group, an optionally substituted arylsulfonyloxy group or a halogen atom.

The sulfonylating agent includes a variety of conventional sulfonylating agents which can convert a hydroxyl group into an alkylsulfonyloxy or arylsulfonyloxy group, for example, an optionally substituted alkylsulfonyl halide or an optionally substituted arylsulfonyl halide.

As the optionally substituted alkylsulfonyl halide and the optionally substituted arylsulfonyl halide, those corresponding to X may be employed. Such optionally substituted alkylsulfonyl halide include, for instance, an alkylsulfonyl halide having 1 to 4 carbon atoms which may be substituted with a substituent such as a halogen atom on the alkyl group, including methanesulfonyl chloride, methanesulfonyl bromide, ethanesulfonyl chloride, ethanesulfonyl bromide, trichloromethanesulfonyl chloride, trifluoromethanesulfonyl chloride, and the like. Examples of the optionally substituted arylsulfonyl halide include an arylsulfonyl halide having 6 to 20 carbon atoms, preferably 6 to 15 carbon atoms, which may have a substituent such as an alkyl group, a nitro group and a halogen atom on the aromatic ring, for example, benzenesulfonyl chloride, benzenesulfonyl bromide, o-toluenesulfonyl chloride, p-toluenesulfonyl chloride, p-toluenesulfonyl bromide, m-nitrobenzenesulfonyl chloride, p-nitrobenzenesulfonyl chloride, p-chlorobenzenesulfonyl chloride, p-bromobenzenesulfonyl chloride, naphthalenesulfonyl chloride and so on.

The reaction of the (S)-1-phenyl-2-propanol derivative of the general formula (III) with the sulfonylating agent can be carried out, usually in the presence of a base at a temperature of, for instance, about −20° C. to 100° C., preferably about −10° C. to 40° C., and more preferably about 0° C. to 30° C. When the reaction temperature is lower than −20° C., the reaction rate is decreased, and when the reaction temperature exceeds 100° C., occurrence of a side reaction tends to be enhanced.

The base includes inorganic bases and organic bases. As examples of the inorganic bases, there may be mentioned alkali metal hydroxides such as sodium hydroxide, potassium hydroxide and lithium hydroxide; alkaline earth metal hydroxides such as magnesium hydroxide, calcium hydroxide and barium hydroxide; alkali metal carbonates such as sodium carbonate, potassium carbonate and lithium carbonate; alkaline earth metal carbonate such as magnesium carbonate, calcium carbonate and barium carbonate; alkali metal hydrogencarbonates such as sodium hydrogencarbonate and potassium hydrogencarbonate. The organic bases include, for example, metal alkoxides such as alkali metal alkoxides (for example, a sodium or potassium $C_{1-4}$ alkoxide such as sodium methoxide, sodium ethoxide, sodium propoxide, sodium butoxide, potassium methoxide, potassium ethoxide, potasium propoxide and potassium butoxide, etc.); primary amines such as an alkylamine (e.g. a $C_{1-8}$ alkylamine such as methylamine, ethylamine, propylamine, butylamine, etc.); secondary amines such as chain amines including an dialkylamine (e.g. a di-$C_{1-8}$ alkylamine such as dimethylamine, diethylamine, dipropylamine, diisopropylamine, dibuthylamine, diisobutylamine, di-s-butylamine, di-t-butylamine, dipentylamine, dihexylamine, diheptylamine, dioctylamine, etc.), and cyclic amines such as pipecoline, piperidine, morpholine, pyrrolidine, etc.; tertiary amines such as a trialkylamine (e.g. a tri-$C_{1-8}$ alkylamine such as trimethylamine, triethylamine, tripropylamine, tributylamine, etc.), alkanolamines such as N,N-di-$C_{1-4}$ alkyl alkanolamine (e.g. N,N-dimethylethanolamine, and the like), N,N-dimethylaniline, 4-dimethylaminopyridine, N-methylmorpholine, N-methylpiperidine, and others; nitrogen-containing heterocycric compounds such as pyridine, quinoline, picoline, and others. As the base, the organic bases such as pyridine may frequently be employed.

The reaction may be conducted in an inert solvent. As the solvent, there may be mentioned, for instance, aromatic hydrocarbons such as benzene, toluene, xylene and ethylbenzene; aliphatic hydrocarbons such as pentane, hexane, heptane and octane; alicyclic hydrocarbons such as cyclohexane and methylcyclohexane; halogenated hydrocarbons such as carbon tetrachloride, chloroform, dichloromethane and 1,2-dichloroethane; ethers such as diethyl ether, dibutyl ether, dioxane and tetrahydrofuran; ketones such as acetone and methyl ethyl ketone; esters such as methyl acetate and ethyl acetate; aprotic polar solvents such as acetonitrile, N,N-dimethylformamide and dimethyl sulfoxide.

The using amount of the sulfonylating agent can be selected from a suitable range depending on the reaction rate and economic factors, and is usually about 0.9 gram equivalent or more, preferably about 0.9 to 1.5 gram equivalents and more preferably about 1.1 to 1.3 gram equivalents, relative to 1 gram equivalent of the (S)-1-phenyl-2-propanol derivative of the general formula (III).

By the reaction of the (S)-phenyl-2-propanol derivative with the sulfonylating agent, the corresponding (S)-2-alkylsulfonyloxy-1-phenylpropane derivative or (S)-2-arylsulfonyloxy-1-phenylpropane derivative can selectively be produced with a good yield.

As the halogenating agent, there may be mentioned, for instance, conventional halogenating agents usable when halogenating an optically active alcohol wherein a hydroxyl group is bonded to an asymmetric carbon with retention of the configuration. Examples of such halogenating agents include thionyl chloride, thionyl bromide and the like.

The reaction of the (S)-1-phenyl-2-propanol derivative with the halogenating agent can be carried out at a temperature of, for example, about −20° C. to 150° C. and preferably about 10° C. to 120° C. The reaction conducted at a temperature lower than −20° C. decreases the reaction rate, and the reaction carried out at a temperature exceeding 150° C. tends to cause a side reaction. The reaction may be conducted in an inert solvent. The solvent exemplified as above can also be used in this reaction. The preferred solvent includes a solvent, which advantageously proceed the reaction with retention of the configuration, for example, a solvent containing an oxygen atom or a sulfur atom such as ethers including, for instance, dioxane, diethyl ether, dipropyl ether, diisopropyl ether, 1,2-dimethoxyethane, anisole, tetrahydrofuran, and the like. The halogenating agent can also be used as the solvent.

The amount of the halogenating agent relative to 1 gram equivalent of the (S)-1-phenyl-2-propanol derivative of the general formula (III) is, for instance, about 0.9 gram equivalent or more and preferably about 0.9 to 1.5 gram equivalents. In order to proceed the reaction smoothly, a reaction accelerator such as sodium chloride, sodium bromide and N,N-dimethylformamide; the above mentioned base or the like can be added to the reaction system.

By the reaction of the (S)-1-phenyl-2-propanol derivative of the general formula (III) and the halogenating agent, the corresponding (S)-2-halo-1-phenylpropane derivative can selectively and efficiently be produced.

The (S)-1-phenyl-2-substituted propane derivative of the general formula (IV) produced by the sulfonylation or halogenation as mentioned above can be recovered by conventional separation and purification procedures. For example, the (S)-1-phenyl-2-substituted propane derivative having a high optical purity can be easily obtained by subjecting the reaction mixture to the conventional purification procedure such as pH adjustment or control of the reaction mixture, extraction with an organic solvent, crystallization, recrystallization, vacuum concentration, column chromatography and distillation.

The (S)-1-phenyl-2-substituted propane derivative of the general formula (IV) thus obtained can advantageously be employed as an intermediate for synthesis of the (R,R)-1-phenyl-2-[(2-phenyl-1-methylethyl)amino] ethanol derivative usable as a medicinal compound or an intermediate thereof.

In the (S)-1-phenyl-2-substituted propane derivatives of the general formula (I), (c) other compounds than the compounds of the general formula (III) or (IV), that is, the compounds wherein X is a hydroxyl group which is protected by a protective group can readily or easily be obtained by protecting the hydroxyl group of the compound of the general formula (II) with the protective group in accordance with a conventional manner using a protective reagent. The compound thus obtained can appropriately be used when the protection of the hydroxyl group is required in chemical reaction for producing another derivative from the compound of the general formula (I).

In the (S)-1-phenyl-2-substituted propane derivatives of the general formula (I) of the present invention, $R^1$, $R^2$ or both can be converted from one substituent to another by a conventional technique.

For example, the (S)-1-phenyl-2-substituted propane derivative of the general formula (I) where $R^1$ and $R^2$ are both methyl groups can easily be converted to the compound where $R^1$ and $R^2$ incorporatively form the group shown by the formula (IX) in accordance with the following scheme.

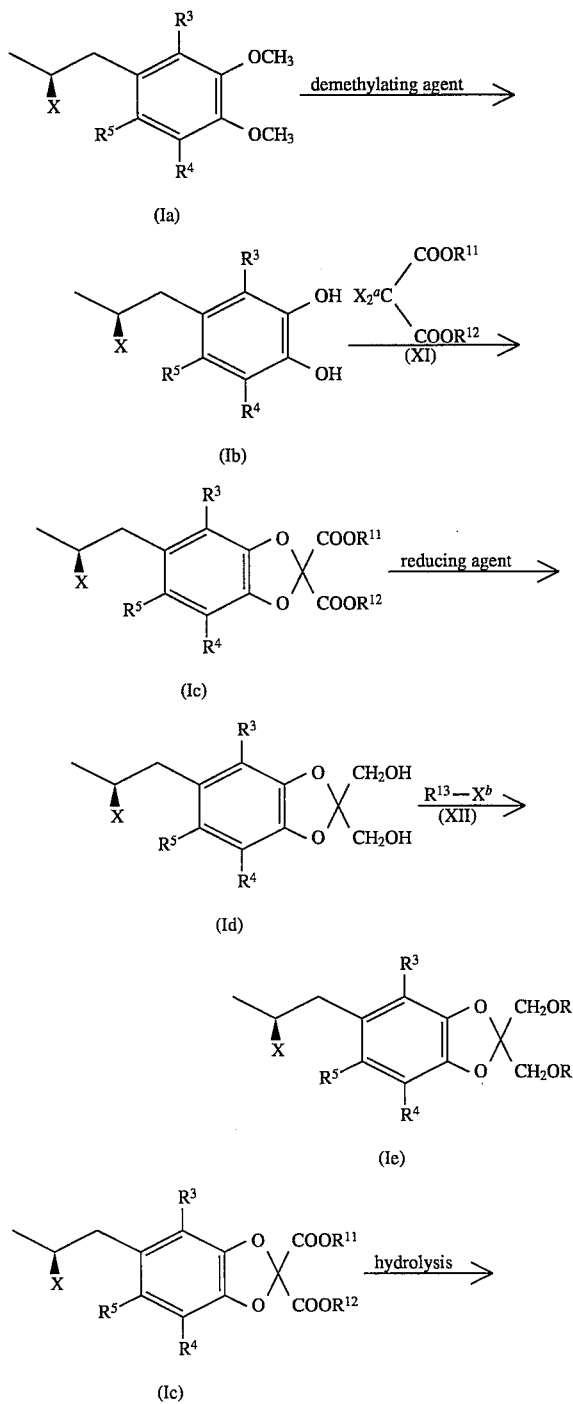

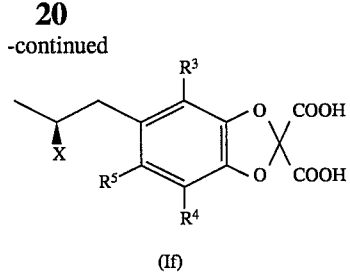

wherein $R^{11}$, $R^{12}$ and $R^{13}$ respectively represent an optionally substituted alkyl group; $X^a$ and $X^b$ are independently a halogen atom; and $R^3$, $R^4$, $R^5$ and X have the same meanings as defined above.

In the reaction, a compound of the formula (Ic) having the group of the formula (IX) where $R^a$ and $R^b$ are both optionally substituted alkoxycarbonyl groups, can be prepared by allowing a demethylating agent such as $BBr_3$ to react with the compound of the general formula (I) where $R^1$ and $R^2$ are both methyl groups, that is, the compound of the formula (Ia), and allowing a dihalomalonic acid ester shown by the formula (XI) such as diethyl dibromomalonate to react with the demethylated compound of the formula (Ib) in the presence of a base such as potassium carbonate. The resultant compound (Ic) can be introduced to a compound of the formula (Id) having the group of the formula (IX) where $R^a$ and $R^b$ are both hydroxyl groups by using a reducing agent such as lithium borohydride. When allowing a halogenated alkyl of the formula (XII) to react with the compound of the formula (Id) in the presence of a base such as sodium hydride, a compound of the formula (Ie) having the group of the formula (XI) where $R^a$ and $R^b$ are respectively an optionally substituted alkoxymethyl group can be obtained.

Further, hydrolysis of the compound of the formula (Ic) in accordance with a conventional hydrolyzing method such as alkali hydrolysis using an alkali including an alkali metal hydroxide (e.g. sodium hydroxide) or the like can easily or readily afford a compound of the formula (If) having the group of the formula (IX) wherein $R^a$ and $R^b$ are, the same or different, a carboxyl group or a salt thereof.

With regard to the method, the disclosures and descriptions in the above mentioned U.S. Pat. No. 5,061,727 and J. Med. Chem., 35, 3081 (1992) can be referred, and these disclosures and descriptions can be incorporated with the disclosure of the present specification.

The process for producing the (R,R)-1-phenyl-2-[(2-phenyl-1-methylethyl)amino]ethanol derivative shown by the general formula (VI) of the present invention is characterized by allowing the (R)-2-amino-1-phenylethanol derivative of the general formula (V) to react with the (S)-1-phenyl-2-substituted propane derivative of the general formula (IV) with inversion in stereochemistry to produce the objective compound of the formula (VI).

The lower alkyl group, lower haloalkyl group, lower alkoxy group or halogen atom in $R^6$, $R^7$, $R^8$, $R^9$ and $R^{10}$ of the general formula (V) may be referred to the lower alkyl group or the like exemplified above. As the substituent $R^9$, a lower haloalkyl group such as a $C_{1-4}$ haloalkyl group, a halogen atom, a nitro group or the like, particularly a halogen atom such as chlorine atom is preferable. Preferred examples of $R^6$, $R^7$, $R^8$ and $R^{10}$ include a hydrogen atom and a $C_{1-4}$ alkyl group, specifically a hydrogen atom.

The protective group for hydroxyl group in Z of the general formula (V) may refer to, for example, a group mentioned as the protective group for hydroxyl group in the explanation for $R^1$, $R^2$ and X.

Typical examples of Z include a hydrogen atom, (A) a group which forms an ether bond with an oxygen atom, particularly, $C_{1-4}$ alkyl group, an optionally substituted 5- to 6-membered heterocyclic group having an oxygen atom or a sulfur atom as a hetero atom, and an optionally substituted silyl group, (B) a group which forms an ester bond with an oxygen atom such as an optionally substituted $C_{1-6}$ acyl group, an optionally substituted $C_{7-16}$ acyl group having an aromatic ring and an optionally substituted acyl group having a heterocyclic ring, and (C) a group which forms a carbonate with an oxygen atom such as an optionally substituted $C_{2-5}$ alkoxycarbonyl group, an optionally substituted $C_{8-20}$ aralkyloxycarbonyl group and an optionally substituted $C_{7-20}$ aryloxycarbonyl group. Particularly, a hydrogen atom can advantageously be used as Z.

In the present invention, the protective group for hydroxyl group, introduction of the protective group to hydroxyl group and cleavage of the protective group may, for example, be referred to and incorporated with "Protective Groups in Organic Synthesis" (T. W. Greene, A Wiley-Interscience Publication, John Wiley & Sons (1981)).

As practical examples of the (R) -2-amino-1-phenylethanol derivative shown by the general formula (V), there may be mentioned (a) (R)-2-amino-1-phenylethanol; (b) an (R)-2-amino-1-(3-nitrophenyl) ethanol derivative such as (R)-2-amino-1-(3-nitrophenyl) ethanol, (R)-2-amino-1-(2-methyl-3-nitrophenyl)ethanol, etc.; (c) an (R)-2-amino-1-(3-halophenyl) ethanol derivative such as (R)-2-amino-1-(3-chlorophenyl) ethanol, (R)-2-amino-1-(2,3-dichlorophenyl)ethanol, (R)-2-amino-1-(3,4-dichlorophenyl)ethanol, (R)-2-amino-1-(3-bromophenyl)ethanol, (R)-2-amino-1-(2,3-dibromophenyl)ethanol, (R)-2-amino-1-(3,4-dibromophenyl) ethanol, (R)-2-amino-1-(3-fluorophenyl) ethanol, (R)-2-amino-1-(2,3-difluorophenyl)ethanol, (R)-2-amino-1-(3,4-difluorophenyl)ethanol and the like; (d) an (R)-2-amino-1-(3-$C_{1-4}$ haloalkyl-phenyl)ethanol derivative such as (R)-2-amino-1-(3-chloromethylphenyl)ethanol, (R)-2-amino-1-[3-(2-chloroethyl)phenyl]ethanol, (R)-2-amino-1-[3-(4-chlorobutyl)phenyl]ethanol, (R)-2-amino-1-(3-trichloromethylphenyl) ethanol, (R)-2-amino-1-(3-trifluoromethylphenyl)ethanol, (R)-2-amino-1-[3-(1,1,2,2,2-pentafluoroethyl)phenyl]ethanol, etc.; (e) an (R)-2-amino-1-(3-$C_{1-4}$ alkoxy-phenyl)ethanol derivative such as (R)-2-amino-1-(3-methoxyphenyl) ethanol, (R)-2-amino-1-(3-methoxy-4-chlorophenyl)ethanol, (R)-2-amino-1-(3-methoxy-4-methylphenyl)ethanol, (R)-2-amino-1-(3-ethoxyphenyl)ethanol; (f) an (R)-2-amino-1-(3-$C_{1-4}$ alkyl-phenyl)ethanol derivative such as (R)-2-amino-1-(3-methylphenyl) ethanol, (R)-2-amino-1-(3-ethylphenyl)ethanol, (R)-2-amino-1-(3-propylphenyl)ethanol, (R)-2-amino-1-(3-t-butylphenyl)ethanol, etc.; (g) an (R)-2-amino-1-(2-substituted phenyl)ethanol derivative such as (R)-2-amino-1-(2-chlorophenyl)ethanol, (R)-2-amino-1-(2-bromophenyl) ethanol, (R)-2-amino-1-(2-fluorophenyl) ethanol, (R)-2-amino-1-(2-trifluoromethylphenyl)ethanol, (R)-2-amino-1-(2-methoxyphenyl)ethanol, (R)-2-amino-1-(2-ethoxyphenyl)ethanol, (R)-2-amino-1-(2-methylphenyl)ethanol, (R)-2-amino-1-(2-ethylphenyl)ethanol), (R)-2-amino-1-(2-propylphenyl)ethanol, (R)-2-amino-1-(2-t-butylphenyl)ethanol and the like; (h) an (R)-2-amino-1-(4-substituted phenyl)ethanol derivative such as (R)-2-amino-1-(4-chlorophenyl) ethanol, (R)-2-amino-1-(4-bromophenyl) ethanol, (R)-2-amino-1-(4-fluorophenyl)ethanol, (R)-2-amino-1-(4-trifluoromethylphenyl)ethanol, (R)-2-amino-1-(4-methoxyphenyl)ethanol, (R)-2-amino-1-(4-ethoxyphenyl)ethanol, (R)-2-amino-1-(4-methylphenyl)ethanol, (R)-2-amino-1-(4-ethylphenylethanol), (R)-2-amino-1-(4-propylphenyl)ethanol, (R)-2-amino-1-(4-t-butylphenyl)ethanol, and so on.

The (R)-2-amino-1-phenylethanol derivative of the general formula (V) can be obtained by, for instance, subjecting the corresponding racemic 2-amino-1-phenylethanol derivative to a conventional optical resolution. For example, the compound can readily be obtained by allowing an optically active carboxylic acid such as an amino acid (e.g. D-alanine) derivative where the amino group is protected (e.g. N-(t-butoxycarbonyl)-D-alanine, etc.) to react with the racemic derivative to form a diastereomeric salt and recrystallizing the objective compound from the salt. The racemic 2-amino-1-phenylethanol derivative can be prepared by a conventional manner, for instance, allowing a trialkylsilylcyanide such as trimethylsilylcyanide to react with the corresponding benzaldehyde derivative in the presence of a Lewis acid such as anhydrous aluminum chloride to produce an o-trialkylsilylmandelonitrile derivative such as o-trimethylsilylmandelonitrile derivative, subjecting the resultant compound to treatment with a reducing agent such as sodium borohydride and to hydrolysis with an acid, and, when necessary, protecting the hydroxyl group with a suitable protective group.

The reaction of the compound of the general formula (V) and the compound of the general formula (IV) can be carried out, by selecting a reagent, a catalyst and reaction conditions in a suitable range as far as the reaction can be proceeded with inversion of the configuration, and, for example, at about 0° to 150° C. and preferably about 20° to 120° C. If the reaction temperature is lower than 0° C., the reaction rate is decreased, and if it exceeds 150° C., a side reaction is liable to occur.

The reaction may preferably be carried out in the presence of a base. A use of the base may increase the optical purity of the object compound. As the base, the base mentioned above can be employed. Prefered examples of the base include organic bases, particularly secondary amines and tertiary amines. Among them, chain secondary amines, specifically dialkylamines such as di-$C_{1-8}$ alkylamines can advantageously be employed. When such dialkylamine is used, the yield of the objective compound can remarkably be increased. Further, among cyclic amines as above, use of such amines which are bulky, for example pipecoline, may occasionally afford a high yield of the compound.

The amount of the base is, for example, about 0.5 to 10 gram equivalents, preferably about 1.0 to 5 gram equivalents and more preferably about 1.2 to 3.5 gram equivalents relative to 1 mol of the compound of the general formula (IV).

The reaction may be conducted in an inert solvent as mentioned above. Preferred examples of the solvent include hydrocarbons such as aromatic hydrocarbons, aliphatic hydrocarbon and alicyclic hydrocarbons.

The amount of the compound of the general formula (IV) can be selected from a suitable range with regard to the reaction rate and economical factors, and is generally about 0.3 to 1.5 gram equivalents and preferably about 0.5 to 1.3 gram equivalents, and more preferably about 0.8 to 1.2 gram equivalents relative to 1 mole of the compound of the general formula (V).

According to this method, the amino group of the (R)-2-amino-1-phenylethanol derivative may attack the carbon atom on the 2-position of the (S)-1-phenyl-2-substituted propane derivative of the general formula (IV) from the opposite direction against the substituent Y, and, thus, a substitution reaction with inversion can smoothly proceed stereoselectively. Therefore, the corresponding (R,R)-1-phenyl-2-[(2-phenyl-1-methylethyl)amino]ethanol derivative of the general formula (VI) or a salt thereof with a by-produced acid HY, wherein Y has the same meaning as defined above, can be produced with a high reaction yield and optical yield.

The (R,R)-1-phenyl-2-[(2-phenyl-1-methylethyl)amino]ethanol derivative and a salt thereof thus obtained can selectively react with the β3-receptor in vivo to decrease or reduce blood sugar significantly and to remarkably restrain or suppress obesity. The pharmacological activity in the (R,R)-isomer is extremely higher than those in the other optical isomers. (R,R)-[disodium 5-[2-[[2-(3-chlorophenyl)-2-hydroxyethyl]amino]propyl]-1,3-benzodioxole-2,2-dicarboxylate] shows, for example, a higher activity than the corresponding (S,S)-enantiomer by a factor of 47 (see the above-mentioned U.S. Patent).

When the corresponding (R)-enantiomer is used instead of the (S)-1-phenyl-2-substituted propane derivative in the reaction, the object compound (R,R)-1-phenyl-2-[(2-phenyl-1-methylethyl)amino]ethanol derivative can hardly be produced. Further, use of the racemic 1-phenyl-2-substituted propane derivative produces the objective compound only with a yield of 50% at most, and an isolating process for isolating and removing a by-produced optical isomer is required.

As described above, the (S)-1-phenyl-2-substituted propane derivative of the present invention is remarkably usable and effective intermediate to selectively obtain the (R,R)-1-phenyl-2-[(2-phenyl-1-methylethyl)amino]ethanol derivative efficiently with a high yield, thus the (S)-enantiomer is remarkably more usable than the corresponding (R)-enantiomer and the racemic form.

Further, the (S)-1-phenyl-2-substituted propane derivative of the formula (I) of the invention, differing from the (R)-1-methyl-2-phenylethylamine derivative, does not have an antihypnotic or arousal action, therefore is easy to handle or treat and suited for a use in commercial production.

$R^1$, $R^2$ or the both of the compound of the general formula (VI) can be converted from one substituent to another by a conventional manner. As such manner, the methods explained in $R^1$ and $R^2$ of the compound of the general formula (I) may be referred to.

For example, (R,R)-1-phenyl-2-[(2-phenyl-1-methylethyl)amino]ethanol derivative of the general formula (VI) where $R^1$ and $R^2$ are both methyl groups can easily be converted to the compound where $R^1$ and $R^2$ incorporatively form the group shown by the formula (IX) in accordance with the above mentioned method. With regard to the method, the disclosures and descriptions in the above mentioned U.S. Pat. No. 5,061,727 and J. Med. Chem., 35, 3081 (1992) can be referred and incorporated with the present specification.

In the reaction, a compound having the group of the formula (IX) where $R^a$ and $R^b$ are both optionally substituted alkoxycarbonyl groups, can be prepared by allowing a demethylating agent such as $BBr_3$ to react with the compound of the general formula (VI) where $R^1$ and $R^2$ are both methyl groups for demethylation, and allowing a dihalomalonic acid ester shown by the formula (XI) such as diethyl dibromomalonate to react with the demethylated compound in the presence of a base such as potassium carbonate. The resultant compound can be introduced to a compound having the group of the formula (IX) where $R^a$ and $R^b$ are both hydroxyl groups by using a reducing agent such as lithium borohydride. When allowing an alkyl halide of the formula (XII) to react with the resulting compound in the presence of a base such as sodium hydride, a compound having the group of the formula (IX) where $R^a$ and $R^b$ are respectively an optionally substituted alkoxymethyl group can be prepared.

Further, hydrolysis of the compound having the group of the formula (IX) where $R^a$ and $R^b$ are respectively an optionally substituted alkoxycarbonyl group, in accordance with a conventional hydrolyzing method such as alkali hydrolysis using an alkali such as an alkali metal hydroxide (e.g. sodium hydroxide) or the like can easily or readily afford a compound having the group of the formula (IX) wherein $R^a$ and $R^b$ are, the same or different, a carboxyl group or a salt thereof.

The (R,R)-1-phenyl-2-[(2-phenyl-1-methylethyl)amino]ethanol derivative of the general formula (VI) or a salt thereof produced in the above-mentioned reaction can be recovered by a conventional isolation and purification technique. For instance, the (R,R)-1-phenyl-2-[(2-phenyl-1-methylethyl)amino]ethanol derivative or a salt thereof having a high optical purity can easily or readily be obtained by subjecting the reaction mixture, if necessary after adjusting to alkaline, to the conventional purification procedure such as extraction with an organic solvent, vacuum concentration, column chromatography, distillation, crystallization and recrystallization.

The (R,R)-1-phenyl-2-[(2-phenyl-1-methylethyl)amino]ethanol derivative or a salt thereof can advantageously be used, as intact or, where necessary, subjected to a suitable chemical modification, as a medicament such as an anti-obesity agent and an anti-diabetic agent. The processes for such chemical modification may be referred to the descriptions and disclosures in, for example, the above-mentioned U.S. Pat. No. 5,061,727, J. Med. Chem., 35, 3081 (1992) and "Protective groups in Organic Synthesis" (T. W. Greene, A Wiley-Interscience Publication, John Wiley & Sons (1981)).

The (R)-1-phenyl-2-substituted propane derivative shown by the general formula (VII) and production thereof are illustrated hereinbelow.

As examples and preferred $R^1$ to $R^5$ and X of the general formula (VII), there may be mentioned the substituents as mentioned above for the general formula (I).

Among (R)-1-phenyl-2-substituted propane derivatives of the general formula (VII), preferred examples include compounds where $R^1$ and $R^2$ are, the same or different, (i) a hydrogen atom, a $C_{1-4}$ alkyl group (specifically a methyl group) or (ii) $R^1$ and $R^2$ incorporatively form an optionally substituted methylene group of the formula (IX) wherein $R^a$ and $R^b$ are respectively a carboxyl group or a salt thereof, or a $C_{2-5}$ alkoxycarbonyl group; $R^3$, $R^4$, and $R^5$ are independently a hydrogen atom or a $C_{1-4}$ alkyl group; and X is a hydroxyl group, a $C_{1-2}$ alkylsulfonyloxy group, a $C_{6-15}$ arylsulfonyloxy group or a halogen atom.

Practical examples of the (R)-1-phenyl-2-substituted propane derivative shown by the general formula (VII) can refer the examples of the corresponding (S)-1-phenyl-2-substituted propane derivative of the general formula (I) as mentioned above. Such examples include (1) an (R)-1-(3,4-dihydroxyphenyl)-2-substituted propane derivative, (2) an (R)-1-(3,4-di-$C_{1-4}$ alkoxyphenyl)-2-substituted propane derivative, (3) an (R)-1-(2,2-di-$C_{1}$alkyl-1,3-benzodioxol-5-yl)-2-substituted propane derivative, (4) an (R)-1-[2,2-bis($C_{2-5}$ alkoxycarbonyl)-1,3-benzodioxol-5-yl]-2-substituted propane derivative and (5) an (R)-1-(2,2-dicarboxy-1,3-benzodioxol-5-yl)-2-substituted propane derivative.

As the (1) (R)-1-(3,4-dihydroxyphenyl)-2-substituted propane derivative, there may be mentioned, for instance, (R)-1-(3,4-dihydroxyphenyl)-2-propanol, (R)-[2-(3,4-dihydroxyphenyl)-1-methylethyl p-toluenesulfonate], (R)-[2-(3,4-dihydroxyphenyl)-1-methylethyl methanesulfonate], (R)-2-chloro-1-(3,4-dihydroxyphenyl)propane, (R)-2-bromo-1-(3,4-dihydroxyphenyl)propane and the like.

Examples of the (2) (R)-1-(3,4-di-$C_{1-4}$ alkoxyphenyl)-2-substituted propane derivative include (R)-1(3,4-dimethoxyphenyl)-2-propanol, (R)-[2-(3,4-dimethoxyphenyl)-1-methylethyl p-toluenesulfonate], (R)-[2-(3,4-dimethoxyphenyl)-1-methylethyl methanesulfonate], (R)-2-chloro-1-(3,4-dimethoxyphenyl)propane, (R)-2-bromo-1-(3,4-dimethoxyphenyl)propane and so on.

The (3) (R)-1-(2,2-di-$C_{1-4}$ alkyl-1,3-benzodioxol-5-yl)-2-substituted propane derivative includes, for example, (R)-1-(2,2-dimethyl-1,3-benzodioxol-5-yl)-2-propanol, (R)-[1-methyl-2-(2,2-dimethyl-1,3-benzodioxol-5-yl)ethyl p-toluenesulfonate], (R)-[1-methyl-2-(2,2-dimethyl-1,3-benzodioxol-5-yl)ethyl methanesulfonate], (R)-2-chloro-1-(2,2-dimethyl-1,3-benzodioxol-5-yl)propane, (R)-2-bromo-1-(2,2-dimethyl-1,3-benzodioxol-5-yl)propane, etc.

As examples of the (4) (R)-1-[2,2-bis ($C_{2-5}$ alkoxycarbonyl)-1,3-benzodioxol-5-yl]-2-substituted propane derivative, there may be mentioned (R)-[dimethyl 5-(2-hydroxypropyl)-1,3-benzodioxole-2,2-dicarboxylate], (R)-[diethyl 5-(2-hydroxypropyl)-1,3-benzodioxole-2,2-dicarboxylate], (R)-[dimethyl 5-[2-(p-toluenesulfonyloxy)propyl]-1,3-benzodioxole-2,2-dicarboxylate], (R)-[diethyl 5-[2-(p-toluenesulfonyloxy)propyl]-1,3-benzodioxole-2,2-dicarboxylate], (R)-[dimethyl 5-[2-(methanesulfonyloxy)propyl]-1,3-benzodioxole-2,2dicarboxylate], (R)-[diethyl 5-[2-(methanesulfonyloxy)propyl]-1,3-benzodioxole-2,2-dicarboxylate], (R)-[dimethyl 5-(2-chloropropyl)-1,3-benzodioxole-2,2-dicarboxylate], (R)-[diethyl 5-(2-chloropropyl)-1,3-benzodioxole-2,2-dicarboxylate], (R)-[dimethyl 5-(2-bromopropyl)-1,3-benzodioxole-2,2-dicarboxylate], (R)-[diethyl 5-(2-bromopropyl)-1,3-benzodioxole-2,2-dicarboxylate] and the like.

Examples of the (5) (R)-1-(2,2-dicarboxy-1,3-benzodioxol-5-yl)-2-substituted propane derivative include (R)-[disodium 5-[2-(hydroxypropyl)-1,3-benzodioxole-2,2-dicarboxylate], (R)-[disodium 5-[2-(p-toluenesulfonyloxy)propyl]-1,3-benzodioxole-2,2dicarboxylate], (R)-[disodium 5-[2-(methanesulfonyloxy)propyl]-1,3-benzodioxole-2,2-dicarboxylate], (R)-[disodium 5-(2-chloropropyl)-1,3-benzodioxole-2,2-dicarboxylate], (R)-[disodium 5-(2-bromopropyl)-1,3-benzodioxole-2,2-dicarboxylate] and others.

The (R)-1-phenyl-2-substituted propane derivative of the general formula (VII) can be prepared by a variety of methods, for example, those mentioned in the (S)-1-phenyl-2-substituted derivative of the general formula (I) can be referred, and the object compound of the formula (VII) can advantageously be produced with the use of an action of a microorganism or a preparation thereof.

For example, the (R)-1-phenyl-2-substituted propane derivative shown by the general formula (VII) where X is a hydroxyl group, that is the compound of the formula (VII'), can readily be obtained by permitting a microorganism or a preparation thereof to act on the phenylacetone derivative of the general formula (II) to asymmetrically reduce and harvesting or recovering the product optically active (R)-1-phenyl-2-substituted propane derivative.

Any strain of microorganism that is capable of asymmetrically reducing the phenylacetone derivative of the general formula (II) to produce the optically active (R)-1-phenyl-2-substituted propanol derivative (VII') can be used in the method.

Examples of such microorganism include a strain of microorganisms belonging to the genus *Corynebacterium*, the genus *Xanthomonas*, the genus *Micrococcus*, the genus *Botryoascus* and the genus *Candida*.

(75) The strain of microorganism belonging to the genus *Corynebacterium* includes *Corynebacterium variabilis* JCM 2154, etc.

(76) The strain of microorganism belonging to the genus *Xanthomonas* includes *Xanthomonas* sp. IFO 3085, etc.

(77) The strain of microorganism belonging to the genus *Micrococcus* includes *Micrococcus luteus* AHU 1427, etc.

(78) The strain of microorganism belonging to the genus *Botryoascus* includes *Botryoascus synaedendrus* IFO 1604, etc.

(79) The strain of microorganism belonging to the genus *Candida* includes *Candida parapsilosis* IFO 0585, etc.

For producing the optically active (R)-1-phenyl-2substituted propane derivative of the formula (VII), any of wild strains, mutants and recombinant strains which can be obtained by a genetic engineering technique such as cell fusion or gene manipulation can preferably be employed, as far as having the above mentioned ability or capability.

The strains of microorganisms each designated by IFO, JCM or AHU numbers can be available from the above-identified organizations.

The cultivation of the microorganism, asymmetric reduction and recovery of the reaction product can be conducted by similar manners as in the production of the (S)-1-phenyl-2-substituted propane derivative of the general formula (III).

In the (R)-1-phenyl-2-substituted propane derivative of the general formula (VII), $R^1$ and $R^2$ can be converted from one substituent to another by a conventional manner similarly in the compound (I).

The (R)-1-phenyl-2-substituted propane derivative of the formula (VII) may be converted to the (S)-1-phenyl-2-substituted propane derivative of the formula (I) by, for example, subjecting the (R)-enantiomer to nucleophilic substitution reaction accompanied with a steric inversion. Such reaction can be conducted with the use of a nucleophilic reagent for introducing X or a group convertible to X to produce a sterically inverted (S)-enantiomer.

The (R)-1-phenyl-2-substituted propane derivative where X is a hydroxyl group, that is, the compound of the general formula (VII') can easily be converted to the (S)-1-phenyl-2-substituted propane derivative of the general formula (I) wherein X is a hydroxyl group or a halogen atom, namely, the compound shown by the general formula (VIII) by selecting an reagent, a catalyst and reaction conditions from a suitable range wherein the reaction is proceeded with steric inversion. For example, the reaction can be carried out in accordance with the following scheme:

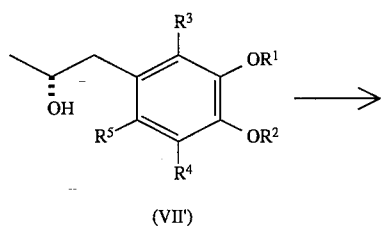

(VII')

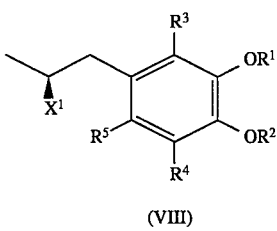

(VIII)

In the general formula (VIII), $X^1$ represents a hydroxyl group or a halogen atom. The halogen atom includes halogen atoms as mentioned above.

The conversion of the compound of the general formula (VII') to the compound of the general formula (VIII) wherein $X^1$ is a hydroxyl group can be carried out by, for example, the following method according to Mitsunobu reaction.

The (S)-1-phenyl-2-substituted propane derivative of the general formula (VIII) wherein $X^1$ is a hydroxyl group can be obtained by allowing an organic acid to react with the compound of the general formula (VII') in the presence of triarylphosphine (e.g. triphenylphosphine, etc.) and an azodicarboxylic acid ester such as ethyl azodicarbonate to form the sterically inverted corresponding organic acid ester, and hydrolyzing the resulting ester. The organic acid includes, for example, formic acid, acetic acid, trichloroacetic acid, trifluoroacetic acid, benzoic acid and the like. The formation of the organic acid ester may be conducted, for example, at a temperature of about −60° C. to 60° C. The reaction may be carried out in an inert solvent such as an aromatic hydrocarbon (for example, benzene, toluene and so on) and an ether (e.g. tetrahydrofuran, etc.). The proportions of triarylphosphine, organic acid and azodicarboxylic acid ester based on 1 mole of the compound of the general formula (VII') are respectively about 0.7 to 2.0 moles. The hydrolysis of the organic acid ester can be conducted by a conventional manner such as acid-hydrolysis or alkali-hydrolysis.

Such method utilizing Mitsunobu reaction wherein an optically active alcohol is sterically inverted to the corresponding optically active alcohol may refer to methods or those analogous thereto described, for example, in Synthesis, 1 (1981); Tetrahedron Lett., 1619 (1973); and Bull. Chem. Soc. Jpn., 44, 3427 (1971), and these descriptions can be incorporated to the present specification.

For the conversion of the optically active alcohol to the corresponding enantiomer, following methods can also be applied:

(a) the method comprising esterifying an optically active alcohol to a carboxylic acid ester such as trichloroactic acid ester, and hydrolyzing the resultant carboxylic acid ester, in a water-ether solvent such as 75% $H_2O$-dioxane, can also be applied (see Chem. Lett., 1976, 893), and (b) the method which comprises (a) converting an optically active alcohol to a sulfonic acid ester such as p-toluenesulfonic acid ester, (b) allowing an organic acid salt such as tetraethylammonium acetate and sodium acetate (-acetic acid) to react with the resulting sulfonic acid ester to sterically invert to the corresponding organic acid ester, and (c) hydrolyzing the resultant organic acid ester (J. Am. Chem. Soc., 87, 3682, (1965); and J. Chem. Soc., 1954, 965).

The (S)-1-phenyl-2-substituted propane derivative of the general formula (VIII) wherein $X^1$ is a halogen atom can be prepared from the compound of the formula (VII') by choosing a reagent, a catalyst, a solvent, and other reaction conditions from an adequate range as far as the reaction may be conducted with sterically inverting.

The conversion of the compound of the general formula (VII') to the compound of the general formula (VIII) wherein $X^1$ is a halogen atom can be carried out, for example, by the following procedure (J. Chem. Soc., 1709 (1953); and J. Chem. Soc., 3795 (1954)).

The reaction can be carried out by allowing a halogenating agent such as phosphorus pentachloride, phosphorus pentabromide, thionyl chloride and thionyl bromide to react with the compound of the general formula (VII') in the presence of a base such as the inorganic base (e.g. calcium carbonate) and the organic base as mentioned above to invert the compound sterically. The halogenation may be carried out, for instance, at about −20° C. to 150° C. The reaction may be conducted in an inert solvent such as an aromatic hydrocarbon (for instance, benzene, toluene and the like) and a halogenated hydrocarbon (e.g. methylene chloride, chloroform and so on). Where thionyl chloride or thionyl bromide is employed, the reaction may frequently be carried out in the presence of a base as exemplified above, or an organic base may frequently be used as the solvent to improve the inversion rate. Examples of such organic base include amines such as triethylamine, N,N-dimethylaniline and N-methylpiperidine; and nitrogen-containing heterocyclic compounds such as pyridine and picoline.

The proportion of the halogenating agent relative to 1 gram equivalent of the (R)-1-phenyl-2-propanol derivative of the general formula (VII'), is, for example, about 0.9 gram equivalent or more, and preferably about 0.9 to 1.5 gram equivalents. A reaction accelerator such as sodium chloride, sodium bromide and N,N-dimethylformamide may be added to the reaction system in order to proceed the reaction steadily or smoothly.

For the conversion of the (R)-1-phenyl-2-substituted propane derivative of the general formula (VII') to the (S)-1-phenyl-2-substituted propane derivative of the general formula (I) where X is a halogen atom, the following descriptions in literatures can also be referred and incorporated into the present specification:

(1) the method allowing a methanesulfonyl halide (e.g. methanesulfonyl chloride) to react with an optically active alcohol in the presence of a base and lithium halide such as lithium chloride (J. Org. Chem., 56, 2769 (1991)), (2) the method comprising allowing a p-toluenesulfonyl halide (e.g. p-toluenesulfonyl chloride) to react with an optically active alcohol in the presence of a base to produce a p-toluenesulfonic acid ester and allowing the resultant ester to react with a tetraalkylammonium halide such as tetraalkylammonium chloride (Tetrahedron Lett., 3425 (1990)), (3) the method allowing an N,N-dialkyl-1,2,2-trihalovinylamine (e.g. N,N-diethyl-1,2,2-trichlorovinylamine) to react with an optically active alcohol (J. Am. Chem. Soc., 82, 909 (1960)), (4) the method where a tetraalkyl-kα-halogenoenamine (for instance, tetramethyl-α-chloroenamine) to react with an optically active alcohol (Tetrahedron Lett., 30, 3077 (1989)), (5) the method allowing gaseous hydrochloric acid to react with a mixture of an optically active alcohol and nitrile to convert a halogenated compound via an imidate (J. Am. Chem. Soc., 77, 2341 (1955); Ber. Deutsch Chem. Ges., 92, 370 (1959); and Tetrahedron Lett., 2517 (1970)), (6) the method where a carbon tetrahalide such as carbon tetrachloride and carbon tetrabromide is allowed to react with an optically active alcohol in the presence of triphenylphosphine (J. Org. Chem., 56, 3009 (1991); and Chem. Ind (London), 1017 (1969)), (7) the method allowing an azodicarboxylic acid ester such as ethyl azodicarbonate, and a methyl halide such as methyl bromide to react with an optically active alcohol in the presence of triphenylphosphine (Tetrahedron, 39, 2591 (1983)), (8) the method allowing a zinc halide (e.g. zinc chloride), an azodicarboxylic acid ester (for instance, ethyl azodicarbonate) and triphenylphosphine to react with an optionally active alcohol (J. Org. Chem., 49, 3027 (1984); Tetrahedron Lett., 28, 4199 (1987); and Herb. Chem. Acta, 32, 184 (1949)), (9) the method which comprises allowing a 2-dialkylamino N,N'-diphenyl-1,3,2-diazaphosphorane such as 2-dimethylamino N,N'-diphenyl-1,3,2-diazaphosphorane to react with an optically active alcohol to produce a corresponding 2-alkoxy N,N'-diphenyl-1,3,2-diazaphosphorane and allowing a halogenating agent (e.g. sulfuryl chloride, bromine, methyl iodide, etc.) to react with the resulting compound (Tetrahedron Lett., 23, 4411 (1982)), and

(10) the method where 3-alkyl-2-fluorobenzothiazolium tetrafluoroborate such as 3-ethyl-2-fluorobenzothiazolium tetrafluoroborate to react with an optically active alcohol in the presence of a metal halide such as sodium chloride, sodium bromide, sodium iodide, lithium chloride, lithium bromide and lithium iodide (Chem. Lett., 619 (1976)).

The obtained (S)-1-phenyl-2-substituted propane derivative of the general formula (VIII) is an specifically important intermediate for production of the (R,R)-1-phenyl-2-[(2-phenyl-1-methylethyl)amino]ethanol derivative. Accordingly, the (R)-1-phenyl-2-substituted propane derivative of the general formula (VII) of the present invention is remarkably usable as an intermediate material for the (S)-1-phenyl-2-substituted propane derivative.

The methods for conversion of the (R)-1-phenyl-2-substituted propane derivative of the general formula (VII) to the (S)-1-phenyl-2-substituted propane derivative of the general formula (I) can also be applied to the conversion of the corresponding (S)-enantiomer to the (R)-enantiomer.

The following examples are intended to illustrate the invention in further detail and should by no means be construed as delimiting the scope of the invention.

EXAMPLES

The quantitative determination and optical purity determination of 1-(3,4-dimethoxyphenyl)-2-propanol in the reaction mixture were carried out by subjecting the reaction mixture to high performance liquid chromatography using an optical resolution column (column: Chiralcel OF (trade name), Daicel Chemical Industries, Ltd.; solvent: n-hexane/2-propanol=90/10; flow rate: 1 ml/min.; temperature: 40° C.; wavelength: 220 nm).

Examples 1 to 139 [Production of (S)-1-(3,4-dimethoxyphenyl)-2-propanol]

YM Medium (0.3% by weight of yeast extract, 0.3% by weight of malt extract, 0.5% by weight of peptone, 2% by weight of glucose, pH 6.0) was used for strains of microorganism belonging to yeasts, and PM medium (2% by weight of glucose, 0.3% by weight of peptone, 0.5% by weight of yeast extract, 0.3% by weight of meat extract, 0.2% by weight of ammonium sulfate, 0.1% by weight of potassium dihydrogenphosphate, 0.05% by weight of magnesium sulfate, pH 7.0) was used for strains of microorganism belonging to bacteria.

A test tube of diameter of 21 mm was charged with 5 ml of the above mentioned medium respectively. After sterilization, the tube was inoculated with one of the following microbial strains. The inoculated tube was incubated under shaking at 30° C. for 24 hours.

Example 1: *Sphingobacterium* sp. IFO 13310
Example 2: *Aeromonas hydrophila* subsp. *proteolytiga* IFO 13287
Example 3: *Agrobacterium radiobacter* IFO 12664
Example 4: *Aureobacterium testaceum* IFO 12675
Example 5: *Bacillus cereus* AHU 1355
Example 6: *Cellulomonas flavigena* IFO 3754
Example 7: *Chromobacterium iodinum* IFO 3558
Example 8: *Corynebacterium aquaticum* IFO 12154
Example 9: *Gluconobacter oxydans* IFO 3255
Example 10: *Jensenia canicruria* IFO 13914
Example 11: *Comamonas acidovorans* IFO 13582
Example 12: *Pseudomonas fluorescens* IFO 3081
Example 13: *Pseudomonas putida* IFO 3738
Example 14: *Alternaria japonica* IFO 5244
Example 15: *Amanita citrina* IFO 8261
Example 16: *Aspergillus awamori nakazawa* IFO 4033
Example 17: *Aspergillus ficuum* IFO 4018
Example 18: *Aspergillus niger* AHU 7105
Example 19: *Aspergillus niger* IFO 5374
Example 20: *Cochliobolus miyabeanus* IFO 6631
Example 21: *Corynespora cassiicola* IFO 6724
Example 22: *Dactylium dendroides* ATCC 46032
Example 23: *Drechslera avenae* IFO 6636
Example 24: *Echinopodospora jamaicensis* IFO 9819
Example 25: *Gelasinospora cerealis* IFO 6759
Example 26: *Gonatobotryum apiculatum* IFO 9098
Example 27: *Helminthosporium sigmoideum* var. *irregulare* IFO 5273
Example 28: *Mortierella isabelina* IFO 6336
Example 29: *Paecilomyces variotii* IFO 4855
Example 30: *Phialophora pedrosoi* IFO 6071
Example 31: *Phytophthora capsici* IFO 8386
Example 32: *Podospora carbonaria* IFO 30294
Example 33: *Rhizomucor pusillus* IFO 4578
Example 34: *Septoria glycines* IFO 5294
Example 35: *Sporormiella isomera* IFO 8538
Example 36: *Stemphylium sarciniforme* IFO 7243
Example 37: *Talaromyces flavus* var. flavus IFO 7231
Example 38: *Torula jeanselmei* IFO 6857
Example 39: *Ustilago cynodontis* IFO 7530
Example 40: *Westerdykella multispora* IFO 5813
Example 41: *Ambrosiozyma cicatricosa* IFO 1846
Example 42: *Ambrosiozyma monospora* IFO 1965
Example 43: *Dekkera custersianus* IFO 1585
Example 44: *Candida aaseri* IFO 10104
Example 45: *Candida atomspherica* IFO 1969
Example 46: *Candida beechii* IFO 10229
Example 47: *Candida diversa* IFO 1091
Example 48: *Candida ergatensis* IFO 10233
Example 49: *Candida fluviatilis* IFO 10234
Example 50: *Candida fusiformate* IFO 10225
Example 51: *Candida glabrata* IFO 0622
Example 52: *Candida gropengiesseri* IFO 0659
Example 53: *Candida halonitratophila* IFO 1595
Example 54: *Candida inconspicua* IFO 0621
Example 55: *Candida kefyr* DSM 70073
Example 56: *Candida krusei* DSM 70075
Example 57: *Candida lambica* DSM 70090
Example 58: *Candida mogii* IFO 0436
Example 59: *Candida maltosa* IFO 1978
Example 60: *Candida melibiosica* IFO 10238

Example 61: *Candida membranaefaciens* IFO 1246
Example 62: *Candida oleophila* JCM 2444
Example 63: *Candida parapsilosis* IFO 1022
Example 64: *Candida pintolopesii* var. *pintolopesii* IFO 0729
Example 65: *Candida pseudointermedia* IFO 1693
Example 66: *Candida catenulata* DSM 70136
Example 67: *Candida rugosa* IFO 0591
Example 68: *Candida saitoana* IFO 0768
Example 69: *Candida sake* IFO 1149
Example 70: *Candida natalensis* IFO 1981
Example 71: *Candida salmanticensis* IFO 10242
Example 72: *Candida santamariae* IFO 1982
Example 73: *Candida schatavii* IFO 10258
Example 74: *Candida shehatae* IFO 1983
Example 75: *Candida silvanorum* IFO 10419
Example 76: *Candida sorbophila* IFO 1583
Example 77: *Candida tenuis* IFO 10315
Example 78: *Candida utilis* IFO 0396
Example 79: *Candida utilis* IFO 0988
Example 80: *Candida albicans* IFO 0759
Example 81: *Clavispora lusitaniae* IFO 1019
Example 82: *Cryptococcus humicolus* IFO 0760
Example 83: *Cryptococcus neoformans* IAM 4788
Example 84: *Debaryomyces varijiae* DSM 70252
Example 85: *Galactomyces reessii* IFO 1112
Example 86: *Filobasidium capsuligenum* IFO 1119
Example 87: *Geotrichum candidum* IFO 4598
Example 88: *Geotrichum fermentans* JCM 2467
Example 89: *Geotrichum fragrans* JCM 2450
Example 90: *Hansenula polymorpha* ATCC 26012
Example 91: *Hansenula capsulata* DSM 70269
Example 92: *Hansenula glucozyma* DSM 70271
Example 93: *Hansenula wickerhamii* DSM 70280
Example 94: *Issatchenkia scutulata* var. *scutulata* IFO 10070
Example 95: *Kloeckera africana* IFO 0869
Example 96: *Kluyveromyces lactis* IFO 0433
Example 97: *Kluyveromyces marxianus* DSM 70800
Example 98: *Kluyveromyces polysporus* DSM 70294
Example 99: *Leucosporidium scottii* IFO 1924
Example 100: *Lodderomyces elongisporus* IFO 1676
Example 101: *Metschnikowia bicuspidata* IFO 1408
Example 102: *Metschnikowia pulcherrima* DSM 70336
Example 103: *Metschnikowia reukaufii* DSM 70880
Example 104: *Myxozyma lipomycoides* IFO 10350
Example 105: *Oosporidium margaritiferum* IFO 1208
Example 106: *Pachysolen tannophilus* IFO 1007
Example 107: *Pichia cellobiosa* DSM 2147
Example 108: *Pichia farinosa* IFO 1163
Example 109: *Pichia lindnerii* DSM 70718
Example 110: *Pichia ohmeri* DSM 70815
Example 111: *Pichia thermotolerans* IFO 10025
Example 112: *Pichia pastoris* DSM 70382
Example 113: *Pichia trehalophila* DSM 70391
Example 114: *Pichia carsonii* DSM 70392
Example 115: *Pichia subpelliculosa* IFO 0808
Example 116: *Malassezia furfur* IFO 0656
Example 117: *Rhodosporidium diobovatum* IFO 1830
Example 118: *Rhodosporidium toruloides* IFO 1638
Example 119: *Kondoa malvinella* IFO 1936
Example 120: *Rhodotorula glutinis* AHU 3454
Example 121: *Rhodotorula rubra* IFO 0383
Example 122: *Saccharomyces rouxii* IAM 0487
Example 123: *Octosporomyces octosporus* IFO 0353
Example 124: *Sporidiobolus johnsonii* IFO 6903
Example 125: *Sporidiobolus pararoseus* IFO 1104
Example 126: *Sporidiobolus salmonicolor* IFO 1845
Example 127: *Sporobolomyces pararoseus* IFO 1036
Example 128: *Sporopachydermia lactativora* IFO 1867
Example 129: *Sterigmatomyces elviae* DSM 70852
Example 130: *Torulaspora delbrueckii* IFO 0381
Example 131: *Torulopsis nemodendra* DSM 70647
Example 132: *Trigonopsis variabilis* IFO 0755
Example 133: *Wickerhamia fluorescens* DSM 70715
Example 134: *Wickerhamiella domercquii* IFO 1857
Example 135: *Wingea robertsii* IFO 1277
Example 136: *Zygoascus hellenicus* IFO 1575
Example 137: *Zygosaccharomyces bailii* IFO 0468
Example 138: *Zygosaccharomyces bisporus* DSM 70415
Example 139: *Zygozyma oligophaga* IFO 10360

The cells were isolated by centrifuging and suspended in 1 ml of 0.1M phosphate buffer (pH 7.0) containing 0.5% by weight of 3,4-dimethoxyphenylacetone and 5% by weight of glucose. A test tube of 21 mm diameter was charged with the suspension and reaction was conducted on a reciprocating shaker at 30° C. for 48 hours.

After completion of the reaction, the reaction suspension was added with a small amount of sodium chloride and extracted with 5 ml of n-hexane. The n-hexane extract was subjected to determination and the optical purity and the yield of the product 1-(3,4-dimethoxyphenyl)-2-propanol were determined. The results are set forth in Tables 1 to 7.

TABLE 1

| Example No. | (S)-1-(3,4-dimethoxyphenyl)-2-propanol | |
|---|---|---|
| | Yield (%) | Optical purity (% e.e.) |
| 1 | 39.5 | 29.1 |
| 2 | 29.2 | 94.6 |
| 3 | 10.9 | 91.8 |
| 4 | 42.0 | 94.3 |
| 5 | 18.8 | 92.7 |
| 6 | 16.2 | 77.2 |
| 7 | 11.7 | 23.0 |
| 8 | 43.0 | 47.9 |
| 9 | 20.3 | 98.6 |
| 10 | 22.4 | 92.3 |
| 11 | 10.3 | 90.2 |
| 12 | 14.1 | 77.0 |
| 13 | 10.0 | 94.5 |
| 14 | 10.8 | 80.9 |
| 15 | 12.4 | 85.6 |
| 16 | 13.8 | 79.8 |
| 17 | 10.0 | 98.6 |
| 18 | 15.0 | 83.3 |
| 19 | 15.2 | 80.4 |
| 20 | 15.6 | 67.3 |

TABLE 2

| Example No. | (S)-1-(3,4-dimethoxyphenyl)-2-propanol | |
|---|---|---|
| | Yield (%) | Optical purity (% e.e.) |
| 21 | 11.2 | 88.9 |
| 22 | 13.8 | 92.4 |
| 23 | 11.0 | 95.8 |
| 24 | 21.0 | 98.0 |
| 25 | 26.0 | 94.4 |
| 26 | 13.8 | 67.0 |
| 27 | 14.8 | 98.3 |
| 28 | 17.2 | 96.2 |
| 29 | 32.0 | 93.9 |
| 39 | 11.4 | 84.9 |

TABLE 2-continued

| Example No. | (S)-1-(3,4-dimethoxy-phenyl)-2-propanol | |
|---|---|---|
| | Yield (%) | Optical purity (% e.e.) |
| 31 | 28.4 | 96.7 |
| 32 | 10.6 | 82.4 |
| 33 | 15.0 | 92.0 |
| 34 | 12.8 | 91.0 |
| 35 | 12.8 | 64.2 |
| 36 | 13.2 | 69.7 |
| 37 | 15.0 | 93.9 |
| 38 | 26.4 | 25.9 |
| 39 | 11.8 | 94.7 |
| 40 | 18.2 | 72.2 |

TABLE 3

| Example No. | (S)-1-(3,4-dimethoxy-phenyl)-2-propanol | |
|---|---|---|
| | Yield (%) | Optical purity (% e.e.) |
| 41 | 28.4 | 98.8 |
| 42 | 22.2 | 97.0 |
| 43 | 12.2 | 95.6 |
| 44 | 43.4 | 97.7 |
| 45 | 24.6 | 93.8 |
| 46 | 19.0 | 92.0 |
| 47 | 14.9 | 66.2 |
| 48 | 37.5 | 38.3 |
| 49 | 34.3 | 69.4 |
| 59 | 15.4 | 79.0 |
| 51 | 18.5 | 93.3 |
| 52 | 21.4 | 66.7 |
| 53 | 15.8 | 76.9 |
| 54 | 10.6 | 77.5 |
| 55 | 35.2 | 99.2 |
| 56 | 17.2 | 66.2 |
| 57 | 47.1 | 98.6 |
| 58 | 19.2 | 80.2 |
| 59 | 21.9 | 19.1 |
| 60 | 15.7 | 96.2 |

TABLE 4

| Example No. | (S)-1-(3,4-dimethoxy-phenyl)-2-propanol | |
|---|---|---|
| | Yield (%) | Optical purity (% e.e.) |
| 61 | 40.8 | 81.6 |
| 62 | 25.2 | 76.4 |
| 63 | 22.4 | 85.0 |
| 64 | 10.7 | 84.2 |
| 65 | 10.7 | 57.0 |
| 66 | 10.3 | 89.3 |
| 67 | 21.6 | 89.3 |
| 68 | 21.5 | 98.2 |
| 69 | 69.1 | 96.9 |
| 69 | 12.9 | 20.6 |
| 71 | 10.5 | 79.5 |
| 72 | 38.6 | 84.9 |
| 73 | 23.6 | 83.0 |
| 74 | 18.4 | 83.0 |
| 75 | 37.7 | 92.3 |
| 76 | 10.4 | 83.6 |
| 77 | 10.1 | 65.3 |
| 78 | 26.3 | 96.9 |
| 79 | 42.9 | 97.6 |
| 80 | 34.2 | 87.0 |

TABLE 5

| Example No. | (S)-1-(3,4-dimethoxy-phenyl)-2-propanol | |
|---|---|---|
| | Yield (%) | Optical purity (% e.e.) |
| 81 | 69.5 | 94.2 |
| 82 | 16.7 | 77.8 |
| 83 | 13.8 | 97.2 |
| 84 | 25.5 | 98.3 |
| 85 | 24.1 | 99.2 |
| 86 | 29.8 | 99.1 |
| 87 | 12.3 | 99.4 |
| 88 | 18.0 | 95.0 |
| 89 | 17.5 | 98.2 |
| 90 | 66.1 | 97.3 |
| 91 | 34.0 | 99.0 |
| 92 | 44.7 | 86.6 |
| 93 | 25.8 | 76.5 |
| 94 | 10.2 | 75.5 |
| 95 | 14.8 | 53.0 |
| 96 | 27.9 | 96.4 |
| 97 | 40.9 | 93.0 |
| 98 | 22.1 | 92.2 |
| 99 | 35.0 | 95.9 |
| 100 | 33.8 | 62.1 |

TABLE 6

| Example No. | (S)-1-(3,4-dimethoxy-phenyl)-2-propanol | |
|---|---|---|
| | Yield (%) | Optical purity (% e.e.) |
| 101 | 39.6 | 79.4 |
| 102 | 25.6 | 90.9 |
| 103 | 13.1 | 78.6 |
| 104 | 38.4 | 99.0 |
| 105 | 14.8 | 52.9 |
| 106 | 24.6 | 96.3 |
| 107 | 15.4 | 78.6 |
| 108 | 34.9 | 92.8 |
| 109 | 71.3 | 97.9 |
| 110 | 17.0 | 76.9 |
| 111 | 16.9 | 97.4 |
| 112 | 71.3 | 97.9 |
| 113 | 28.2 | 97.8 |
| 114 | 19.3 | 90.1 |
| 115 | 13.3 | 98.5 |
| 116 | 13.9 | 78.2 |
| 117 | 29.9 | 96.4 |
| 118 | 86.3 | 98.4 |
| 119 | 23.7 | 77.0 |
| 120 | 10.4 | 96.8 |

TABLE 7

| Example No. | (S)-1-(3,4-dimethoxy-phenyl)-2-propanol | |
|---|---|---|
| | Yield (%) | Optical purity (% e.e.) |
| 121 | 24.0 | 73.9 |
| 122 | 33.0 | 97.7 |
| 123 | 58.8 | 69.2 |
| 124 | 64.4 | 97.4 |
| 125 | 12.6 | 94.8 |
| 126 | 18.3 | 94.3 |
| 127 | 19.9 | 95.2 |
| 128 | 38.4 | 99.0 |
| 129 | 26.7 | 78.0 |
| 130 | 57.1 | 98.3 |
| 131 | 10.0 | 85.3 |
| 132 | 11.3 | 85.9 |

TABLE 7-continued

| | (S)-1-(3,4-dimethoxy-phenyl)-2-propanol | |
|---|---|---|
| Example No. | Yield (%) | Optical purity (% e.e.) |
| 133 | 27.9 | 100 |
| 134 | 16.4 | 92.3 |
| 135 | 10.4 | 95.2 |
| 136 | 34.2 | 94.8 |
| 137 | 11.5 | 93.9 |
| 138 | 23.4 | 93.2 |
| 139 | 32.6 | 96.3 |

Example 140 [Production of (S)-1-(3,4-dimethoxyphenyl)-2-propanol]

A 2.6-liter mini jar fermenter was charged with 1.5 liter of YM media of the same composition as mentioned in Examples 1 to 139. After sterilization with the use of an autoclave, the fermenter was inoculated with *Torulaspora delbrueckii* IFO 0381, and the inoculated fermenter was incubated at 30° C., under aeration at 1 vvm, with stirring at 400 rpm for 24 hours. After completion of incubation, the cells were concentrated by centrifuging.

A 2.6-liter mini far fermenter was charged with 1 liter of 0.1M phosphate buffer (pH 7.0) and the obtained cells were suspended therein. To the suspension was added 5 g of 3,4-dimethoxyphenylacetone and 50 g of glucose, and the reaction was carried out at 30° C., under aeration at 1 vvm, with stirring at 400 rpm for 48 hours.

After completion of the reaction, the cells were removed off by centrifuging, and the obtained supernatant was added with 400 g of sodium chloride, and extracted with 1 liter of ethyl acetate three times. The ethyl acetate extract was dried over anhydrous sodium sulfate, and the solvent was removed under reduced pressure to give 3.1 g of an oily substance. The oily substance was purified with the use of silica gel chromatography (eluent: n-hexane/ethyl acetate= 7/3) to give 2.7 g of crystalline (S)-1-(3,4-dimethoxyphenyl)-2-propanol (m.p.: 51° C). The specific rotation of the compound was $[\alpha]_D^{20}$ +28.3° (c=1.06, chloroform). As a result of analyzing the compound by high performance liquid chromatography using an optical resolution column (column: Chiralcel OF (trade name), Daicel Chemical Industries, Ltd.), the optical purity thereof was 100% e.e.

$^1$H-NMR (270 MHz, CDCl$_3$) δ: 1.24 (d, 3H), 1.72 (br, s, 1H), 2.66 (m, 2H), 3.86 (d, 6H), 3.99 (m, 1H), 6.76 (m, 3H)

IR (cm$^-$): 3400, 2880, 1515, 1460, 1260, 1240, 800

The absolute configuration of the obtained 1-(3,4-dimethoxyphenyl)-2-propanol was determined by the following manner.

The 1-(3,4-dimethoxyphenyl)-2-propanol obtained above was subjected to sulfonylation by p-toluenesulfonyl chloride and reacted with benzylamine to give N-benzyl-3,4-dimethoxyamphetamine. The resultant compound was converted into 3,4-dimethoxyamphetamine by hydrogenation decomposition under hydrogen atmosphere with 5% Pd-C.

As a result of the determination of the obtained 3,4-dimethoxyamphetamine, the specific rotation thereof was $[\alpha]_D^{25}$ −26.5° (c=4 58 chloroform).

To an ethanol solution of the 3,4-dimethoxyamphetamine was added an equivalent amount of (half time as much mole of) concentrated sulfuric acid to yield 3,4-dimethoxyamphetamine•½H$_2$SO$_4$ as crystals. The specific rotation of the sulfuric acid salt was $[\alpha]_D^{25}$−19.03° (c=2.27, H$_2$O). The obtained 3,4-dimethoxyamphetamine was determined as an (R)-form since the values in a literature (J. Org. Chem., 22, 33 (1957)) are as follows.

(R)-3,4-dimethoxyamphetamine: $[\alpha]_D$−30.9° (C=4.13, chloroform)

(R)-3,4-dimethoxyamphetamine • ½H$_2$SO$_4$: $[\alpha]_D$−21.4° (C=2.0, H$_2$O)

Since the reaction where 3,4-dimethoxyamphetamine is produced from 1-(3,4-dimethoxyphenyl)-2-propanol is accompanied by inversion, the 1-(3,4-dimethoxyphenyl)-2-propanol obtained above was proved to be an (S)-enantiomer.

Example 141 [Production of (S)-[2-(3,4-dimethoxyphenyl)-1-methylethyl p-toluenesulfonate]

To a solution of 404 mg of (S)-1-(3,4-dimethoxyphenyl)-2-propanol in 2 ml of pyridine was added 472 mg of p-toluenesulfonyl chloride under nitrogen atmosphere on an ice bath. The mixture was stirred at 20° C. for 17 hours. Granules of ice were added to the mixture to cease the reaction, and the reaction mixture was stirred for further 30 minutes. The reaction mixture was acidified by adding 2N hydrochloric acid and was extracted twice with 20 ml of chloroform. The organic extract was washed with a saturated aqueous solution of sodium chloride, dried over anhydrous magnesium sulfate, distilled off the solvent to give 716 mg of (S)-[2-(3,4-dimethoxyphenyl)-1-methylethyl p-toluenesulfonate] as white crystals (yield: 98%). Analysis of the compound by high performance liquid chromatography using an optical resolution column (column: Chiralcel OF (trade name), Daicel Chemical Industries, Ltd. ) revealed that the optical purity thereof was 100% e.e.

m.p.: 62.4° to 62.8° C. $[\alpha]_D^{25}$+20.6° (c=1.0 chloroform)

IR (KBr) (cm$^{-1}$): 3044, 2995, 2937, 1594, 1517, 1357, 1346, 1262, 1243, 1187, 1178, 1169, 1157, 1142, 1029, 913, 889, 854, 806, 766, 666, 578, 558

$^1$H-NMR (500 MHz, CDCl$_3$) δ 1.34 (d, 3H), 2.41 (s, 3H), 2.73 (dd, 1H), 2.83 (dd, 1H), 3.76 (s, 3H), 3.86 (s, 3H), 4.70 (m, 1H), 6.47 (d, 1H), 6.59 (m, 1H), 6.69 (d, 1H), 7.24 (d, 2H), 7.57 (d, 2H)

$^{13}$C-NMR (125 MHz, CDCl$_3$) δ: 20.74, 21.49, 42.48, 55.54, 55.76, 80.88, 110.90, 112.21, 121.44, 127.48, 128.80, 129.41, 133.48, 144.19, 147.81, 148.61

Example 142 [Production of (R,R)-1-(3-chlorophenyl)-2-[[2-(3,4-dimethoxyphenyl)-1-methylethyl]amino]ethanol]

(R)-2-Amino-1-(3-chlorophenyl)ethanol (806 mg) was added to (S)-[2-(3,4-dimethoxyphenyl)-1-methylethyl p-toluenesulfonate] (700 mg) under nitrogen atmosphere, and the mixture was stirred at 60° C. for 31 hours. The reaction mixture was adjusted to alkaline by adding a 10% aqueous solution of sodium hydroxide, and extracted twice with 20 ml of chloroform. The organic extract was dried over anhydrous sodium sulfate, subjected to distilling off the solvent and to purifying with silica gel chromatography (eluent: chloroform/methanol) to give 550 mg of (R,R)-1-(3-chlorophenyl)-2-[[2-(3,4-dimethoxyphenyl)-1-methylethyl]amino]ethanol as white crystals (yield: 79%). The NMR spectrum data are shown as follows.

¹H-NMR (500MHz, CDCl₃) δ:1.09 (d, 3H), 2.08 (brs, 2H), 2.61–2.69 (m, 3H), 2.87–2.92 (m, 2H), 3.86 (s, 3H), 3.87 (s, 3H), 4.55 (dd, 1H), 6.68 (s, 1H), 6.70 (d, 1H), 6.80 (d, 1H), 7.18–7.26 (m, 3H), 7.35 (s, 1H)

¹³C-NMR (125 MHz, CDCl₃) δ:20.37, 43.39, 54.09, 54.26, 55.87, 55.89, 71.11, 111.21, 112.36, 121.19, 123.89, 125.94, 127.55, 129.61, 131.56, 134.32, 144.66, 147.57, 148.87

The optical purity of the compound was determined by converting the compound into a corresponding cyclic urethane derivative. That is, the compound was converted into (R,R)-5-(3-chlorophenyl)-3-[2-(3,4-dimethoxyphenyl)-1-methylethyl]-2-oxazolidinone by allowing carbonyldiimidazole and N-methylmorpholine to react with the compound in tetrahydrofuran at room temperature for 2 hours, then heating the mixture under reflux for 3 hours. Analyzing the compound by high performance liquid chromatography using an optical resolution column (column: Chiralcel AS (trade name), Daicel Chemical Industries, Ltd.), the optical purity of the compound was 90% e.e. The NMR spectrum data of the obtained cyclic urethane derivative are set forth hereinbelow.

¹H-NMR (500 MHz, CDCl₃) δ:1.26 (d, 3H), 2.67 (dd, 1H), 2.81 (dd, 1H), 3.24 (dd, 1H), 3.81 (s, 3H), 3.83 (dd, 1H), 3.86 (s, 3H), 4.33 (ddq, 1H), 5.35 (dd, 1H), 6.63 (d, 1H), 6.70 (s, 1H), 6.73 (d, 1H), 6.91 (d, 1H), 7.12 (s, 1H), 7.22 (dd, 1H), 7.28 (d, 1H)

¹³C-NMR (125 MHz, CDCl₃) δ: 17.72, 39.71, 47.69, 49.55, 55.75, 55.79, 73.38, 111.03, 111.75, 120.76, 123.44, 125.56, 128.73, 129.76, 130.07, 134.62, 141.14, 147.71, 148.90, 156.90

Examples 143 to 147 [Production of (R)-1-(3,4-dimethoxyphenyl)-2-propanol]

The cultivating procedures and reaction procedures were conducted in the same manner as in Examples 1 to 139 except for using the following strains of microorganisms. The results are shown in Table 8.

Example 143: *Corynebacterium variabilis* JCM 2154
Example 144: *Xanthomonas* sp. IFO 3085
Example 145: *Micrococcus luteus* AHU 1427
Example 146: *Botryoascus synaedendrus* IFO 1604
Example 147: *Candida parapsilosis* IFO 0585

TABLE 8

| | (R)-1-(3,4-dimethoxy-phenyl)-2-propanol | |
|---|---|---|
| Example No. | Yield (%) | Optical purity (% e.e.) |
| 143 | 12.6 | 74.9 |
| 144 | 18.6 | 83.9 |
| 145 | 19.3 | 53.2 |
| 146 | 20.6 | 34.5 |
| 147 | 31.1 | 10.6 |

Example 148 [Production of (S)-1-(3,4-dimethoxyphenyl)-2-propanol]

(R)-1-(3,4-Dimethoxyphenyl)-2-propanol (0.9 g) was obtained as crystals by cultivation, reaction and purification in the similar manners as in Example 140 except that PM medium was employed instead of YM media and that *Xanthomonas* sp. IFO 3085 was used instead of *Torulaspora delbrueckii* IFO 0381. The crystals gave the same signals in 1H-NMR analysis as in the (S)-1-(3,4-dimethoxyphenyl)-2-propanol obtained in Example 140. Further the specific rotation of the crystals was "–", therefore, the crystals were proved to be (R)-1-(3,4-dimethoxyphenyl)-2-propanol. As a result of determination by high performance liquid chromatography with the use of a optical resolution column, the optical purity of the compound was 85.5% e.e.

Thus obtained (R)-1-(3,4-dimethoxyphenyl)-2-propanol (744 mg, 3.80 mmol.), triphenylphosphine (1196 mg) and formic acid (210 mg) were dissolved in 60 ml of tetrahydrofuran, and to the resultant solution, was added a solution of 794 mg of diethyl azodicarboxylate in 10 ml of tetrahydrofuran. The mixture was stirred at room temperature for 15 hours, and reaction mixture was concentrated under reduced pressure. The resulting residue was subjected to purification by silica gel chromatography (eluent: n-hexane/ethyl acetate=7/3) to give 595 mg of formic acid ester of (S)-1-(3,4-dimethoxyphenyl)-2-propanol. The ester was subjected to alkali-hydrolysis according to a known method and extracted with ethyl acetate, and the solvent was distilled off. The residue was purified by silica gel chromatography (eluent: n-hexane/ethyl acetate=7/3) to give 450 mg of (S)-1-(3,4-dimethoxyphenyl)-2-propanol as crystals. The optical purity of the compound was 99% e.e. by analyzing by high performance liquid chromatography with the use of an optical resolution column.

Example 149 [Production of (R,R)-1-(3-chlorophenyl)-2-[[2-(3,4-dimethoxyphenyl)-1-methylethyl]amino]ethanol]

A mixture of 57.0 g (0. 163 mol) of (S)-[2-(3,4-dimethoxyphenyl)-1-methylethyl p-toluenesulfonate], 33.7 g (0. 196 mol) of (R)-2-amino-1-(3-chlorophenyl)ethanol, 33.7 g (0. 244 tool) of anhydrous potassium carbonate and 133 ml of toluene was stirred at 90° C. for 48 hours under nitrogen atmosphere. The reaction mixture was adjusted to alkaline by adding a 10% aqueous solution of sodium hydroxide and extracted twice with 500 ml of toluene. The toluene extract was dried over anhydrous sodium sulfate, and subjected to distillation of the solvent and to purification with silica gel chromatography to give 34.8 g of 1-(3-chlorophenyl)-2-[[2-(3,4-dimethoxyphenyl)-1-methylethyl]amino]ethanol as white crystals (yield: 61%). As a result of isolating and analyzing the isomers with high performance liquid chromatography using an optical resolution column (column: Chiralpack AD (trade name), Daicel Chemical Industries, Ltd.), the optical purity of the title compound was 86.8% [(R,R)/(R,S)=86.8/13.2].

Example 150 [Production of (R,R)-1-(3-chlorophenyl)-2-[[2-3,4-dimethoxyphenyl)-1-methylethyl]amino]ethanol]

Under nitrogen atmosphere, a mixture of 4.20 g (0.0120 tool) of (S)-[2-(3,4-dimethoxyphenyl)-1-methylethyl p-toluenesulfonate], 2.47 g (0. 0144 mol) of (R)-2-amino-1-(3-chlorophenyl)ethanol and 1.82 g (0.0180 mol) of diisopropylamine was stirred at 60° C. for 48 hours. The reaction mixture was adjusted to alkaline by adding a 10% aqueous solution of sodium hydroxide and extracted twice with 500 ml of toluene. The toluene extract was dried over anhydrous sodium sulfate, and subjected to distillation of the solvent and to purification with silica gel chromatography to give 3.23 g of 1-(3-chlorophenyl)-2-[[2-(3,4-dimethoxyphenyl)-1-methylethyl]amino]ethanol as white crystals (yield: 77%). As a result of isolation and analysis of the isomers by high performance liquid chromatography using an optical resolution column (column: Chiralpack AD (trade name), Daicel Chemical Industries, Ltd.), the optical purity of the objective compound was 92.8% [(R,R)/(R,S)=92.8/7.2].

Example 151 [Production of (R,R)-1-(3-chlorophenyl)-2-[[2-(3,4-dimethoxyphenyl)-1-methylethyl]amino]ethanol]

To 2.5 ml of toluene, were added 701 mg (2.00 mmol) of (S)-[2-(3,4-dimethoxyphenyl)-1-methylethyl p-toluenesulfonate], 412 mg (2.40 mmol) of (R)-2-amino-1-(3-chlorophenyl)ethanol and 207 mg (1.50 retool) of anhydrous potassium carbonate, and the mixture was stirred at 90° C. for 24 hours under nitrogen atmosphere. After adjusted to alkaline by adding a 10% aqueous solution of sodium hydroxide, the reaction mixture was extracted twice with 30 ml of toluene. The toluene extract was dried over anhydrous sodium sulfate and subjected to distillation of the solvent and to purification with silica gel chromatography to afford 313 mg of 1-(3-chlorophenyl)-2-[[2-(3,4-dimethoxyphenyl)-1-methylethyl]amino]ethanol as white crystals (yield: 45%). As a result of isolating and analyzing the isomers with high performance liquid chromatography using an optical resolution column (column: Chiralpack AD (trade name), Daicel Chemical Industries, Ltd.), the optical purity of the title compound was 88.3% [(R,R)/(R,S)= 88.3/11.7].

Example 152 [Production of (R,R)-1-(3-chlorophenyl)-2-[[2-(3,4-dimethoxyphenyl)-1-methylethyl]amino]ethanol]

The procedure of Example 151 was followed except for using 415 mg (3.00 mmol) of anhydrous potassium carbonate to give 431 mg of 1-(3-chlorophenyl)-2-[[2-(3,4-dimethoxyphenyl)-1-methylethyl]amino]ethanol (yield: 62%). The optical purity of the title compound was 87.5% [(R,R)/(R,S)=87.5/12.5].

Examples 153 and 154 [Production of (R,R)-1-(3-chlorophenyl)-2-[[2-(3,4-dimethoxyphenyl)-1-methylethyl]amino]ethanol]

The procedure of Example 151 was repeated except that the reaction was conducted using the solvent at the reaction temperature shown in Table 9. The results are set forth in Table 9.

TABLE 9

| | Solvent | Reaction temperature (°C.) | Yield (%) | Optical purity (%) | (R, R)/(R, S) |
|---|---|---|---|---|---|
| Ex. 153 | n-Octane | 90 | 54 | 88.3 | 88.3/11.7 |
| Ex. 154 | Acetonitrile | 60 | 32 | 74.1 | 74.1/25.9 |

Examples 155 and 156 [Production of (R,R)-1-(3-chlorophenyl)-2-[[2-(3,4-dimethoxyphenyl)-1-methylethyl]amino]ethanol]

The title compound was prepared in the same manner as in Example 151 except that 5 ml of toluene was used and that the bases shown in Table 10 were used instead of anhydrous potassium carbonate. The results are set forth in Table 10.

TABLE 10

| | Base | Yield (%) | Optical purity (%) | (R,R)/(R,S) (%) |
|---|---|---|---|---|
| Ex. 155 | Sodium ethoxide | 44 | 87.9 | 87.9/12.1 |
| Ex. 156 | Diisopropylamine | 65 | 74.6 | 74.6/25.4 |

Example 157 [Production of (R,R)-1-(3-chlorophenyl)-2-[[-2-3,4-dimethoxyphenyl)-1-methylethyl]amino]ethanol]

Under nitrogen atmosphere, 350 mg (1.00 mmol) of (S)-[2-(3,4-dimethoxyphenyl)-1-methylethyl p-toluenesulfonate] was added to 206 mg (1.20 mmol) of (R)-2-amino-1-(3-chlorophenyl)ethanol, and the mixture was stirred at 60° C. for 24 hours. The reaction mixture was added with a 10% aqueous solution of sodium hydroxide to be alkaline, and extracted twice with 30 ml of toluene. The toluene extract was dried over anhydrous sodium sulfate, and subjected to distillation of the solvent and to purification with silica gel chromatography to give 187 mg of 1-(3-chlorophenyl)-2-[[2-(3,4-dimethoxyphenyl)-1-methylethyl]amino]ethanol as white crystals (yield: 54%). As a result of isolating and analyzing the isomers by high performance liquid chromatography using an optical resolution column (column: Chiralpack AD (trade name), Daicel Chemical Industries, Ltd.), the optical purity of the title compound was 95.2% [(R,R)/(R,S)=95.2/4.8].

Example 158 [Production of (R,R)-1-(3-chlorophenyl)-2-[[2-(3,4-dimethoxyphenyl)-1-methylethyl]amino]ethanol]

To 274 mg (1.00 mmol) of (S)-[2-(3,4-dimethoxyphenyl)-1-methylethyl methanesulfonate] was added 206 mg (1.20 mmol) of (R)-2-amino-1-(3-chlorophenyl)ethanol, and the mixture was stirred at 60° C. for 24 hours. The reaction mixture was added with a 10% aqueous solution of sodium hydroxide to be alkaline, and extracted twice with 30 ml of toluene. The toluene extract was dried over anhydrous sodium sulfate, and subjected to distillation of the solvent and to purification with silica gel chromatography to give 161 mg of 1-(3-chlorophenyl)-2-[[2-(3,4-dimethoxyphenyl)-1-methylethyl]amino]ethanol as white crystals (yield: 46%). As a result of isolating and analyzing the isomers by high performance liquid chromatography using an optical resolution column (column: Chiralpack AD (trade name), Daicel Chemical Industries, Ltd. ), the optical purity of the title compound was 95.8% [(R,R)/(R,S)=95.8/4.2].

Example 159 [Production of (R,R)-1-(3-chlorophenyl)-2-[[2-(3,4-dimethoxyphenyl)-1-methylethyl]amino]ethanol]

The procedure of Example 158 was followed, except that 403 mg (2.35 mmol) of (R)-2-amino-1-(3-chlorophenyl)ethanol was used, to give 252 mg of 1-(3-chlorophenyl)-2-[[2-(3,4-dimethoxyphenyl)-1-methylethyl]amino]ethanol (yield: 72%). The optical purity of the title compound was 96.4% [ (R,R)/(R,S)=96.4/3.6].

Example 160 [Production of (R,R)-1-(3-chlorophenyl)-2-[[2-(3,4-dimethoxyphenyl)-1-methylethyl]amino]ethanol]

To 274 mg (1.00 mmol) of (S)-[2-(3,4-dimethoxyphenyl)-1-methylethyl methanesulfonate] were added 206 mg (1.20 mmol) of (R)-2-amino-1-(3-chlorophenyl)ethanol and 194 mg (1.50 mmol) of dibutylamine, and the mixture was stirred at 60° C. for 24 hours under nitrogen atmosphere. The reaction mixture was added with a 10% aqueous solution of sodium hydroxide to be alkaline, and extracted twice with 30 ml of toluene. The toluene extract was dried over anhydrous sodium sulfate, and subjected to distillation of the solvent and to purification with silica gel chromatography to give 190 mg of 1-(3-chlorophenyl)-2-[[2-(3,4-dimethoxyphenyl)-1-methylethyl]amino]ethanol as white crystals (yield: 54%). As a result of isolating and analyzing the isomers by high performance liquid chromatography using an optical resolution column (column: Chiralpack AD (trade name), Daicel Chemical Industries, Ltd.), the optical purity of the objective compound was 95.2% [(R,R)/(R,S)= 95.2/4.8].

Examples 161 to 166 [Production of (R,R)-1-(3-chlorophenyl)2-[[2-(3,4-dimethoxyphenyl]-1-methylethyl]amino]ethanol]

The title compound was prepared in the same manner as in Example 160, except that the reaction was carried out using the base, instead of dibutylamine, at the reaction temperature set forth in Table 11. The results are shown in Table 11.

TABLE 11

| | Base | Reaction temperature (°C.) | Yield (%) | Optical purity (%) | (R,R)/(R,S) (%) |
|---|---|---|---|---|---|
| Ex. 161 | Dibutylamine | 75 | 69 | 86.8 | 86.8/13.2 |
| Ex. 162 | Triethylamine | 60 | 47 | 96.9 | 96.9/3.1 |
| Ex. 163 | Pyridine | 60 | 39 | 98.3 | 98.3/1.7 |
| Ex. 164 | 2-Pipecoline | 60 | 57 | 96.0 | 96.0/4.0 |
| Ex. 165 | N-Methylmorpholine | 60 | 39 | 95.9 | 95.9/4.1 |
| Ex. 166 | N,N-Dimethylethanolamine | 60 | 44 | 95.3 | 95.3/4.7 |

Example167 [Production of (S)-[2-(3.4-dimethoxyphenyl)-1-methylethyl methanesulfonate]

Under nitrogen atmosphere, to a methylene chloride solution (20 ml) of 4.91 g (0.025 mol) of (S)-1-(3,4-dimethoxyphenyl)-2-propanol and 3.79 g (0.038 mol) of triethylamine, was added dropwise a methylene chloride solution (10 ml) of 3.43 g (0.030 mol) of methanesulfonyl chloride under cooling with an ice bath for 30 minutes. The mixture was stirred for one hour, and the reaction was ceased by addition of 2N hydrochloric acid. The reaction mixture was extracted twice with 50 ml of methylene chloride. The methylene chloride extract was washed with a saturated solution of sodium chloride, dried and subjected to distillation of the solvent to give 6.65 g of (S)-[2-(3,4-dimethoxyphenyl)-1-methylethyl methanesulfonate] as crystals (yield: 97%). As a result of the analysis by high performance liquid chromatography using an optical resolution column (column: Chiralpack AS (trade name), Daicel Chemical Industries, Ltd.), the optical purity of the title compound was 100%.

m.p.: 79.5° to 80.3° C. $[\alpha]_D^{25}$+26.5 (c=1.24, chloroform)

IR (KBr) (cm$^{-1}$): 3018, 2973, 2937, 2843, 1607, 1590, 1518, 1469, 1447, 1342, 1265, 1238, 1174, 1148, 1122, 1028, 984, 916, 883, 856, 828, 801, 765, 719, 636, 546, 530, 477

$^1$H-NMR (500 MHz, CDCl$_3$) δ:6.82 (d, 1H), 6.77 (dd, 1H), 6.75 (d, 1H), 4.89 (m, 1H), 3.88 (s, 3H), 3.86 (s, 3H), 2.94 (dd, 1H), 2.85 (dd, 1H), 2.60 (s, 3H), 1.45 (d, 3H)

What is claimed is:

1. An (S)-1-phenyl-2-substituted propane derivative shown by the following formula

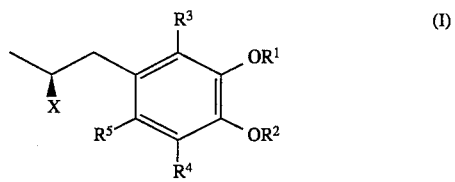

wherein R$^1$ and R$^2$ represent (a) the same or different, a hydrogen atom or a protective group for hydroxyl group, or (b) R$^1$ and R$^2$ may form a 5- to 10-membered ring with the adjacent oxygen atoms;

R$^3$, R$^4$ and R$^5$ independently represent a hydrogen atom, a lower alkyl group, a lower haloalkyl group, a lower alkoxy group, a nitro group or a halogen atom; and X represents (i) a hydroxyl group or hydroxyl group protected with a protective group, (ii) an alkylsulfonyloxy group which may be substituted with a halogen atom, (iii) an arylsulfonyloxy group which may be substituted with a substituent selected from the group consisting of a nitro group, a halogen atom and a C$_{1-4}$ alkyl group, or (iv) a halogen atom.

2. An (S)-1-phenyl-2-substituted propane derivative according to claim 1, wherein (a) R$^1$ and R$^2$ are the same or different, and represent (1) a hydrogen atom, (2) a C$_{1-4}$ alkyl group which may be substituted with a substituent selected from the group consisting of a C$_{1-4}$ alkoxy group, a C$_{1-4}$ alkoxy-C$_{1-4}$ alkoxy group, a C$_{7-20}$ aralkyloxy group, a benzoyl group, a C$_{1-4}$ alkylthio group and a halogen atom, (3) an allyl group, (4) a C$_{3-10}$ cycloalkyl group, (5) a 5- to 6-membered heterocyclic group having an oxygen atom or a sulfur atom as a hetero atom, wherein said heterocyclic group may be substituted with a substituent selected from the group consisting of a halogen atom, a C$_{1-4}$ alkyl group and a C$_{1-4}$ alkoxy group, (6) a C$_{7-20}$ aralkyl group which may be substituted with a substituent selected from the group consisting of a C$_{1-4}$ alkyl group, a halogen atom, a nitro group, a C$_{1-4}$ alkoxy group and a C$_{6-12}$ aryl group, (7) a silyl group which may be substituted with a substituent selected from the group consisting of a C$_{7-20}$ aralkyl group, a C$_{1-4}$ alkyl group, a halogen atom, a nitro group, a C$_{1-4}$ alkoxy group and a C$_{6-12}$ aryl group, (8) an acyl group which may have an aromatic ring or a heterocyclic ring and which may have a substituent selected from the group consisting of a halogen atom, a C$_{1-4}$ alkyl group and a C$_{6-20}$ aryl group, (9) a C$_{2-5}$ alkoxycarbonyl group, (10) a C$_{7-20}$ aryloxycarbonyl group which may be substituted with a substituent selected from the group consisting of a C$_{1-4}$ alkyl group, a nitro group and a halogen atom, (11) a C$_{8-20}$ aralkyloxycarbonyl group which may be substituted with a substituent selected from the group consisting of a C$_{1-4}$ alkoxy group, a C$_{1-4}$ alkyl group, a halogen atom and a nitro group, (12) a C$_{1-4}$ alkylsulfonyl group which may be substituted with a halogen atom or (13) a C$_{6-20}$ arylsulfonyl group which may be substituted with a substituent selected from the group consisting of a nitro group, a halogen atom and a C$_{1-4}$ alkyl group; or (b) $R^1$ and $R^2$ may form a C$_{1-4}$ alkylene group, a carbonyl group or a thiocarbonyl group, Wherein said C$_{1-4}$ alkylene group may be substituted with a substituent selected from the group consisting of a C$_{1-4}$ alkyl group, a C$_{1-4}$ haloalkyl group, a C$_{6-20}$ aryl group which may be substituted with a C$_{1-4}$ alkoxy group or a nitro group, a C$_{1-4}$ alkoxy group, an amino group, a mono- or di- C$_{1-4}$ alkylamino group, a carboxyl group or a salt thereof, a C$_{2-5}$ alkoxycarbonyl group, a hydroxymethyl group and an alkoxymethyl group which may be substituted on the alkyl with a substituent selected from the group consisting of a carboxyl group, a C$_{2-5}$ alkoxycarbonyl group, a hydroxyl group and a C$_{1-4}$ alkoxy group, and wherein when $R^1$ and $R^2$ form a substituted C$_{1-4}$ alkylene group, said substituents for the C$_{1-4}$ alkylene group may form a C$_{5-7}$ cycloalkyl group together with the adjacent carbon atom.

3. An (S)-1-phenyl-1-substituted propane derivative according to claim 2, wherein said C$_{1-4}$ alkylene group formed by $R^1$ and $R^2$ is a group shown by the following formula

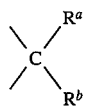 (IX)

wherein
(i) $R^a$ and $R^b$ independently represent a hydrogen atom, a C$_{1-4}$ alkyl group, a C$_{1-4}$ haloalkyl group, a C$_{6-20}$ aryl group which may be substituted with a substituent selected from the group consisting of a C$_{1-4}$ alkoxy group and a nitro group, a C$_{1-4}$ alkoxy group, an amino group, a mono- or di-C$_{1-4}$ alkylamino group, a carboxyl group or a salt thereof, an alkoxycarbonyl group, a hydroxymethyl group and an alkoxymethyl group which may be substituted on the alkyl with a substituent selected from the group consisting of a carboxyl group, a C$_{2-5}$ alkoxycarbonyl group, a hydroxyl group and a C$_{1-4}$ alkoxy group, or
(ii) $R^a$ and $R^b$ may form a C$_{5-7}$ cycloalkyl group with the adjacent carbon atom.

4. An (S)-1-phenyl-2-substituted propane derivative according to claim 1, wherein $R^3$, $R^4$ and $R^5$ independently represent a hydrogen atom, a C$_{1-4}$ alkyl group, a C$_{1-4}$ haloalkyl group, a C$_{1-4}$ alkoxy group, a nitro group or a halogen atom.

5. An (S)-1-phenyl-2-substituted propane derivative according to claim 1, wherein X is (i) a hydroxyl group or a hydroxyl group protected with a protective group selected from the group consisting of (1) a C$_{1-4}$ alkyl group which may be substituted with a substituent selected from the group consisting of a C$_{1-4}$ alkoxy group, a C$_{1-4}$ alkoxy-C$_{1-4}$ alkoxy group, a C$_{7-20}$ aralkyloxy group, a benzoyl group, a C$_{1-4}$ alkylthio group and a halogen atom, (2) an allyl group,
(3) a C$_{3-10}$ cycloalkyl group, (4) a 5- to 6-membered heterocyclic group having an oxygen atom or a sulfur atom as a hetero atom wherein said heterocyclic group may be substituted with a substituent selected from the group consisting of a halogen atom, a C$_{1-4}$ alkyl group and a C$_{1-4}$ alkoxy group, (5) a C$_{7-20}$ aralkyl group which may be substituted with a substituent selected from the group consisting of a C$_{1-4}$ alkyl group, a halogen atom, a nitro group, a C$_{1-4}$ alkoxy group and a C$_{6-12}$ aryl group, (6) a silyl group which may be substituted with a substituent selected from the group consisting of a C$_{7-20}$ aralkyl group, a C$_{1-4}$ alkyl group, a halogen atom, a nitro group, a C$_{1-4}$ alkoxy group and a C$_{6-12}$ aryl group, (7) an acyl group which may have an aromatic ring or a heterocyclic ring and which may have a substituent selected from the group consisting of a halogen atom, a C$_{1-4}$ alkyl group and a C$_{6-20}$ aryl group, (8) a C$_{2-5}$ alkoxycarbonyl group, (9) a C$_{7-20}$ aryloxycarbonyl group which may be substituted with a substituent selected from the group consisting of a C$_{1-4}$ alkyl group, a nitro group and a halogen atom, and (10) a C$_{8-20}$ aralkyloxycarbonyl group which may be substituted with a substituent selected from the group consisting of a C$_{1-4}$ alkoxy group, a C$_{1-4}$ alkyl group, a halogen atom and a nitro group;

(ii) a C$_{1-4}$ alkylsulfonyloxy group which may be substituted with a halogen atom;

(iii) a C$_{6-20}$ arylsulfonyloxy group which may be substituted with a substituent selected from the group consisting of a nitro group, a halogen atom and a C$_{1-4}$ alkyl group; or (iv) a halogen atom.

6. An (S)-1-phenyl-2-substituted propane derivative according to claim 1, wherein (a) $R^1$ and $R^2$ are the same or different, and represents a hydrogen atom, a C$_{1-4}$ alkyl group which may be substituted with a substituent selected from the group consisting of a C$_{1-4}$ alkoxy group, a C$_{1-4}$ alkoxy-C$_{1-4}$ alkoxy group, a C$_{7-20}$ aralkyloxy group, a benzoyl group, a C$_{1-4}$ alkylthio group and a halogen atom, a C$_{7-20}$ aralkyl group Which may be substituted with a substituent selected from the group consisting of a C$_{1-4}$ alkyl group, a halogen atom, a nitro group, a C$_{1-4}$ alkoxy group and a C$_{6-12}$ aryl group or a C$_{1-6}$ acyl group which may be substituted with a halogen atom, or (b) $R^1$ and $R^2$ form a group shown by the following formula

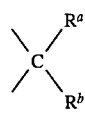 (IX)

wherein
(i) $R^a$ and $R^b$ are, independently, a hydrogen atom, a C$_{1-4}$ alkyl group, a carboxyl group or a salt thereof, a C$_{2-5}$ alkoxycarbonyl group, a hydroxymethyl group or a C4 alkoxy-methyl group which may be substituted with a substituent selected from the group consisting of a carbonyl group, a C$_{2-5}$ alkoxycarbonyl group, a hydroxyl group and a C$_{1-4}$ alkoxy group, or
(ii) $R^a$ and $R^b$ form, together with the adjacent carbon atom, a C$_{5-7}$ cycloalkyl group;

$R^3$, $R^4$ and $R^5$ are, respectively, a hydrogen atom or a C$_{1-4}$ alkyl group; and X is a hydroxyl group, a C$_{1-2}$ alkylsulfonyloxy group which may be substituted with a halogen atom, a C$_{6-15}$ arylsulfonyloxy group which may be substituted with a substituent selected from the group consisting of a nitro group, a halogen atom and a $C_{1-4}$ alkyl group, or a halogen atom.

7. An (R)-1-phenyl-2-substituted propane derivative shown by the following formula

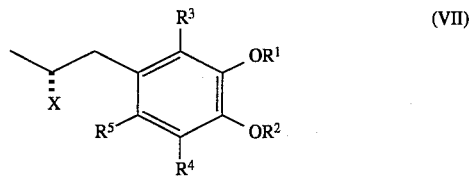

wherein (a) $R^1$ and $R^2$ are the same or different and represents a hydrogen atom or a protective group for a hydroxyl group, or (b) $R^1$ and $R^2$ may form a 5- to 10-membered ring with the adjacent oxygen atoms;

$R^3$, $R^4$ and $R^5$ independently represent a hydrogen atom, a lower alkyl group, a lower haloalkyl group, a lower alkoxy group, a nitro group of a halogen atom; and X represents (i) a hydroxyl group or a hydroxyl group protected with a protective group, (ii) an alkylsulfonyloxy group which may be substituted with a halogen atom, (iii) an arylsulfonyloxy group which may be substituted with a substituent selected from the group consisting of a nitro group, a halogen atom and a $C_{1-4}$ alkyl group, or (iv) a halogen atom.

8. An (R)-1-phenyl-2-substituted propane derivative according to claim 7, wherein (a) $R^1$ and $R^2$ are the same or different and represent (1) a hydrogen atom, (2) a $C_{1-4}$ group which may be substituted with a substituent selected from the group consisting of a $C_{1-4}$ alkoxy group, a $C_{1-4}$ alkoxy-$C_{1-4}$ alkoxy group, a $C_{7-20}$ aralkyloxy group, a benzoyl group, a $C_{1-4}$ alkylthio group and a halogen atom, (3) an allyl group, (4) a $C_{3-10}$ cycloalkyl group, (5) a 5- to 6-membered heterocyclic group having an oxygen atom or a sulfur atom as a hetero atom, wherein said heterocyclic group may be substituted with a substituent selected from the group consisting of a halogen atom, a $C_{1-4}$ alkyl group and a $C_{1-4}$ alkoxy group, (6) a $C_{7-20}$ aralkyl group which may be substituted with a substituent selected from the group consisting of a $C_{1-4}$ alkyl group, a halogen atom, a nitro group, a $C_{1-4}$ alkoxy group and a $C_{6-12}$ aryl group, (7) a silyl group which may be substituted with a substituent selected from the group consisting of a $C_{7-20}$ aralkyl group, a $C_{1-4}$ alkyl group, a halogen atom, a nitro group, a $C_{1-4}$ a $C_{1-4}$ alkoxy group and a $C_{6-12}$ aryl group, (8) an acyl group which may have an aromatic ring or a heterocyclic ring and which may have a substituent selected from the group consisting of a halogen atom, a $C_{1-4}$ alkyl group and a $C_{6-20}$ aryl group, (9) a $C_{2-5}$ alkoxycarbonyl group, (10) a $C_{7-20}$ aryloxcarbonyl group which may be substituted with a substituent selected from the group consisting of a $C_{1-4}$ alkyl group, a nitro group and a halogen atom, (11) a $C_{8-20}$ aralkyloxycarbonyl group which may be substituted with a substituent selected from the group consisting of a $C_{1-4}$ alkoxy group, a $C_{1-4}$ alkyl group, a halogen atom and a nitro group, (12) a $C_{1-4}$ alkylsulfonyl group which may be substituted with a halogen atom or (13) a $C_{6-20}$ arylsulfonyl group which may be substituted with a substituent selected from the group consisting of a nitro group, a halogen atom and a $C_{1-4}$ alkyl group; or (b) $R^1$ and $R^2$ may form a $C_{1-4}$ alkylene group, wherein said $C_{1-4}$ alkylene group may by substituted with a substituent selected from the group consisting of a $C_{1-4}$ alkyl group, a $C_{1-4}$ haloalkyl group, a $C_{6-20}$ aryl group which may be substituted with a $C_{1-4}$ alkoxy group or a nitro group, a $C_1$_alkoxy group, an amino group, amono- or di-$C_{1-4}$ alkylamino group, a carboxyl group or a salt thereof, a $C_{2-5}$ alkoxycarbonyl group, a hydroxymethyl group and an alkoxymethyl group which may be substituted on the alkyl with a substituent selected from the group consisting of a carboxyl group, a $C_{2-5}$ alkoxycarbony group, a hydroxyl group and a $C_{1-4}$ alkoxy group; and wherein when $R^1$ and $R^2$ form a substituted $C_{1-4}$ alkylene group said substituents for the $C_{1-4}$ alkylene group may form a $C_{5-7}$ cycloalkyl group together with the adjacent carbon atom (c) a carbonyl group, a thiocarbonyl group or a group shown by the following formula

wherein $R^a$ and $R^b$ independently represent (i) a hydrogen atom, a $C_{6-20}$ alkyl group, a $C_{1-4}$ haloalkyl group, a $C_{1-4}$ aryl group which may be substituted with a substituent selected from the group consisting of a $C_{1-4}$ alkoxy group and a nitro group, a $C_{1-4}$ alkoxy group, an amino group, a mono-or di-$C_{1-4}$ alkylamino group, a carboxyl group or a salt thereof, an alkoxycarbonyl group, a hydroxymethyl group or an alkoxymethyl group which may be substituted on the alkyl with a substituent selected from the group consisting of a carboxyl group, a $C_{2-5}$ alkoxycarbonyl group, a hydroxyl group and a $C_{1-4}$ alkoxy group, or (ii) $R^a$ and $R^b$ may form a $C_{5-7}$ cycloalkyl group with the adjacent carbon atom;

$R^3$, $R^4$ and $R^5$ independently represent a hydrogen atom, a $C_{1-4}$ alkyl group, a $C_{1-4}$ haloalkyl group, a $C_{1-4}$ alkoxy group, a nitro group or a halogen atom; and X represents (i) a hydroxyl group or hydroxyl group protected with a protective group selected from the group consisting of (1) a $C_1$_alkyl group which may be substituted with a substituent selected from the group consisting of a $C_{1-4}$ alkoxy group, a $C_{1-4}$ alkoxy-$C_{1-4}$ alkoxy group $C_{7-20}$ aralkyloxy group, a benzoyl group, a $C_{1-4}$ alkylthio group and a halogen atom, (2) an alkyl group, (3) a $C_{3-10}$ cycloalkyl group, (4) a5- to 6-membered heterocyclic group having an oxygen atom or a sulfur atom as a hetero atom wherein said heterocyclic group may be substituted with a substituent selected from the group consisting of a halogen atom, a $C_{1-4}$ alkyl group and a $C_{1-4}$ alkoxy group, (5) a $C_{7-20}$ aralkyl group which may be substituted with a substituent selected from the group consisting of a $C_{1-4}$ alkyl group, a halogen atom, a nitro group, a $C_{1-4}$ alkoxy group and a $C_{6-12}$ aryl group, (6) a silyl group which may be substituted with a substituent selected from the group consisting of a $C_{7-20}$ aralkyl group, a $C_{1-4}$ alkyl group, a halogen atom, a nitro group, a $C_{1-4}$ alkoxy group and a $C_{6-12}$ aryl group, (7) an acyl group which may have an aromatic ring or a heterocyclic ring and which may have a substituent selected from the group consisting of a halogen atom, a $C_{1-4}$ alkyl group and a $C_{6-20}$ aryl group, (8) a $C_{2-5}$ alkoxycarbonyl group, (9) a $C_{7-20}$ aryloxycarbonyl group which may be substituted with a substituent selected from the group consisting of a $C_{1-4}$ alkyl group, a nitro group and a halogen atom; and (10) a $C_{8-20}$ aralkyloxycarbonyl group which may be substituted with a substituent selected from the group consisting of a $C_{1-4}$ alkoxy group, a $C_{1-4}$ alkyl group, a halogen atom and a nitro group; (ii) a $C_{1-4}$ alkylsulfonyloxy group which may be substituted with a halogen atom; (iii) a $C_{6-20}$ arylsulfonyloxy group which may be substituted with a substituent selected from the group consisting of a nitro group, a halogen atom and a $C_{1-4}$ alkyl group; or (iv) a halogen atom.

* * * * *